United States Patent [19]

Ung-Chhun et al.

[11] Patent Number: 6,045,701
[45] Date of Patent: Apr. 4, 2000

[54] METHOD OF FILTERING A FLUID SUSPENSION WITH A MEMBRANE HAVING A PARTICULAR COATING

[75] Inventors: Neng S. Ung-Chhun, Lincolnshire; Richard J. Johnson, Mundeline, both of Ill.

[73] Assignee: Baxter International Inc., Deerfield, Ill.

[21] Appl. No.: 09/073,490

[22] Filed: May 6, 1998

Related U.S. Application Data

[63] Continuation-in-part of application No. 08/971,887, Nov. 17, 1997, Pat. No. 5,972,217, which is a continuation-in-part of application No. 08/810,751, Mar. 4, 1997, Pat. No. 5,795,483, which is a division of application No. 08/323,559, Oct. 17, 1994, Pat. No. 5,647,985.

[51] Int. Cl.[7] .......................... B01D 61/00; B01D 61/14
[52] U.S. Cl. .................. 210/650; 210/321.67; 210/321; 210/68; 210/503; 210/504; 210/505; 210/506; 210/508; 210/651
[58] Field of Search ..................... 210/645, 651, 210/503, 504, 505, 506, 507, 508, 321.68, 321.67, 650; 422/101; 427/244, 258, 384, 402, 407.1

[56] References Cited

U.S. PATENT DOCUMENTS

| | | | |
|---|---|---|---|
| 3,945,926 | 3/1976 | Kesting | 210/500.4 |
| 4,053,420 | 10/1977 | Marx | 210/435 |
| 4,130,642 | 12/1978 | Kikygawa et al. | 424/533 |

(List continued on next page.)

FOREIGN PATENT DOCUMENTS

| | | |
|---|---|---|
| 58983/90 | 1/1991 | Australia . |
| 0 370 584 | 5/1988 | European Pat. Off. . |
| 0 397 403 | 11/1990 | European Pat. Off. . |
| 0 406 485 | 1/1991 | European Pat. Off. . |
| 0 408 462 | 1/1991 | European Pat. Off. . |
| 0 419 346 | 3/1991 | European Pat. Off. . |
| 0 500 472 | 9/1993 | European Pat. Off. . |
| 0 561 379 | 9/1993 | European Pat. Off. . |
| 03000 074 | 12/1988 | Japan . |
| 05034337 | 7/1991 | Japan . |
| 05087808 | 9/1991 | Japan . |
| 05148150 | 11/1991 | Japan . |
| 05148151 | 11/1991 | Japan . |
| 4-187206 | 7/1992 | Japan . |
| 5-194243 | 3/1993 | Japan . |
| 9303740 | 3/1993 | WIPO . |
| 9308904 | 5/1993 | WIPO . |

OTHER PUBLICATIONS

Grimm et al., "Glutaraldehyde Affects Biocompatibility of Bioprosthetic Heart Valves," *Surgery*, 1992; vol. 111, No. 1:74–78.

Golomb et al., "The Role of Glutaraldehyde–induced Cross–links in Calcification of Bovine Pericardium Used in Cardiac Valve Bioprostheses," *Amer. J. Pathol.*, 1987; vol. 127, No. 1:122–130.

Levy et al., "Cardiovascular Implant Calcification: a Survey and Update," *Biomaterials*, 1991; vol. 12:707–714.

Harasym et al., "Poly(ethylene glycol)–Modified Phospholipids Prevent Aggregation during Covalent Conjugation of Proteins to Liposomes," *Bioconjugate Chem.*, 1995; vol. 6, No. 2:187–194.

Chen et al., "Effect of 2–amino Oleic Acid Exposure Conditions on the Inhibition of Calcification of Glutaraldehyde Cross–linked Porcine Aortic Valves," *J. Biomed. Mater. Res.*, 1994; vol. 28:1485–1495.

(List continued on next page.)

*Primary Examiner*—John Kim
*Attorney, Agent, or Firm*—Robert Barrett; Bradford R. L. Price; Denise Serewicz

[57] ABSTRACT

Novel blood cell fractionation devices are provided. The device utilizes filters coated with high molecular weight polyethylene oxide derivatives cross-linked to prevent leaching from filter surfaces. These filters have a special efficacy in preventing protein adsorption and cellular adhesion to the membrane filter.

10 Claims, 9 Drawing Sheets

U.S. PATENT DOCUMENTS

| | | | |
|---|---|---|---|
| 4,256,588 | 3/1981 | Hoehn et al. | 210/692 |
| 4,283,289 | 8/1981 | Meyst et al. | 210/448 |
| 4,330,410 | 5/1982 | Takenaka et al. | 210/767 |
| 4,358,476 | 11/1982 | Zimmer et al. | 427/494 |
| 4,399,035 | 8/1983 | Nohmi et al. | 210/500.2 |
| 4,416,777 | 11/1983 | Kuroda et al. | 210/446 |
| 4,596,657 | 6/1986 | Wisdom | 210/206 |
| 4,618,533 | 10/1986 | Steuck | 428/315.7 |
| 4,701,267 | 10/1987 | Watanabe et al. | 210/806 |
| 4,767,541 | 8/1988 | Wisdom | 210/749 |
| 4,810,378 | 3/1989 | Wisdom | 210/206 |
| 4,855,063 | 8/1989 | Carmen et al. | 210/249 |
| 4,880,548 | 11/1989 | Pall et al. | 210/767 |
| 4,915,848 | 4/1990 | Carmen et al. | 210/749 |
| 4,917,799 | 4/1990 | Carmen et al. | 214/425 |
| 4,919,823 | 4/1990 | Wisdom | 210/749 |
| 4,925,572 | 5/1990 | Pall | 210/767 |
| 4,936,993 | 6/1990 | Nomura | 210/446 |
| 4,936,998 | 6/1990 | Nishimura et al. | 210/638 |
| 4,943,287 | 7/1990 | Nishimura et al. | 604/408 |
| 4,976,861 | 12/1990 | Pall | 210/508 |
| 4,977,577 | 12/1990 | Stewart | 210/767 |
| 4,985,153 | 1/1991 | Kuroda et al. | 210/496 |
| 5,034,135 | 7/1991 | Fischel | 210/651 |
| 5,089,146 | 2/1992 | Carmen et al. | 210/206 |
| 5,092,996 | 3/1992 | Spielberg | 210/435 |
| 5,100,551 | 3/1992 | Pall et al. | 210/486 |
| 5,100,564 | 3/1992 | Pall et al. | 210/496 |
| 5,104,788 | 4/1992 | Carmen et al. | 210/516 |
| 5,128,048 | 7/1992 | Stewart et al. | 210/206 |
| 5,190,657 | 3/1993 | Heagle et al. | 210/490 |
| 5,194,145 | 3/1993 | Schoendorfer | 210/90 |
| 5,229,012 | 7/1993 | Pall et al. | 210/767 |
| 5,252,222 | 10/1993 | Matkovish et al. | 210/436 |
| 5,258,126 | 11/1993 | Pall et al. | 210/767 |
| 5,258,127 | 11/1993 | Gsell et al. | 210/767 |
| 5,647,985 | 7/1997 | Ung-Chhun et al. | 210/504 |
| 5,795,483 | 8/1998 | Ung-Chhun et al. | 210/645 |

OTHER PUBLICATIONS

O'Brien et al., "The Metronic Intact Xenograft: an Analysis of 342 Patients over a Seven–year Follow–up Period," *Ann. Thorac Surg.*, 1995; vol. 60(Suppl.):S253–S257.

Breillatt et al., "Recombinant Hirudin Analog Designed for Attachment to Polymers," *Abstract FASEB J.*, 1992, vol. 6:A–1320.

Gendler et al., "Toxic reactions evoked by glutaraldehyde–fixed pericardium and cardiac valve tissue bioprosthesis," *Journal of Biomedical Materials Research*, 1984, vol. 18: 727–736.

Park et al., "Chemical Modification of Implantable Biologic Tissue for Anti–Calcification," *ASAIO Journal*, 1994, vol. 40: M377–M382.

Han et al., "In Vivo Biostability and Calcification–Resistance of Surface–Modified PU–PEO–$SO_3$," *Journal of Biomedical Materials Research*, 1993, vol. 27: 1063–1073.

With : 100<n>225
PEO: R=H
Imidazole-PEO: R=-CO-N⟨imidazole⟩
Tetraamino PEO: R=-CONH(CH$_2$)$_2$NH$_2$
Tetraacrylate PEO: R=-CH=CH$_2$ 1. CH$_3$O(CH$_2$CH$_2$O)$_n$CH$_2$CH$_2$O-R 2. ROCH$_2$CH$_2$O(CH$_2$CH$_2$O)$_n$CH$_2$CH$_2$O-R PEO: R=H
Imidazole-PEO: R=-CO-N⟨imidazole⟩
With : 250<n>450

3.

A= CH$_2$=CH-COO-CH$_2$CH$_2$O(CH$_2$CH2O)$_{77}$

- Uncoated
- 2.5x T-NH2-PEO
- Imz-PEO

CUMULATIVE PLATELETS PRESENTED TO FILTER

- ▫ Uncoated
- ✕ 2.5x T-NH2-PEO
- ☐ Imz-PEO

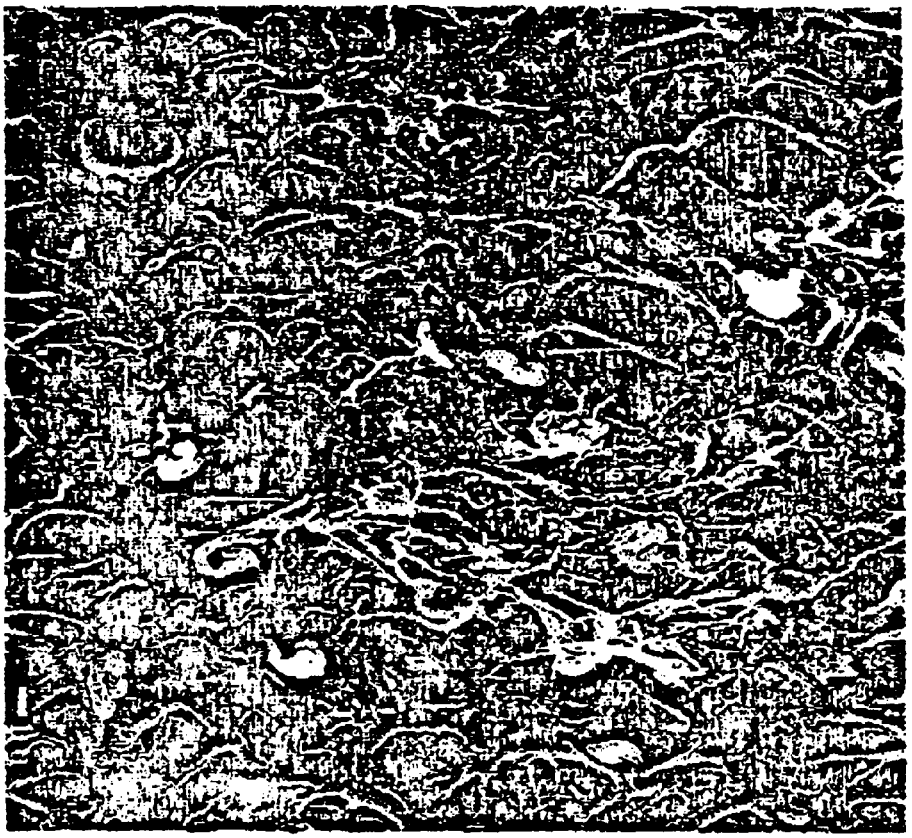
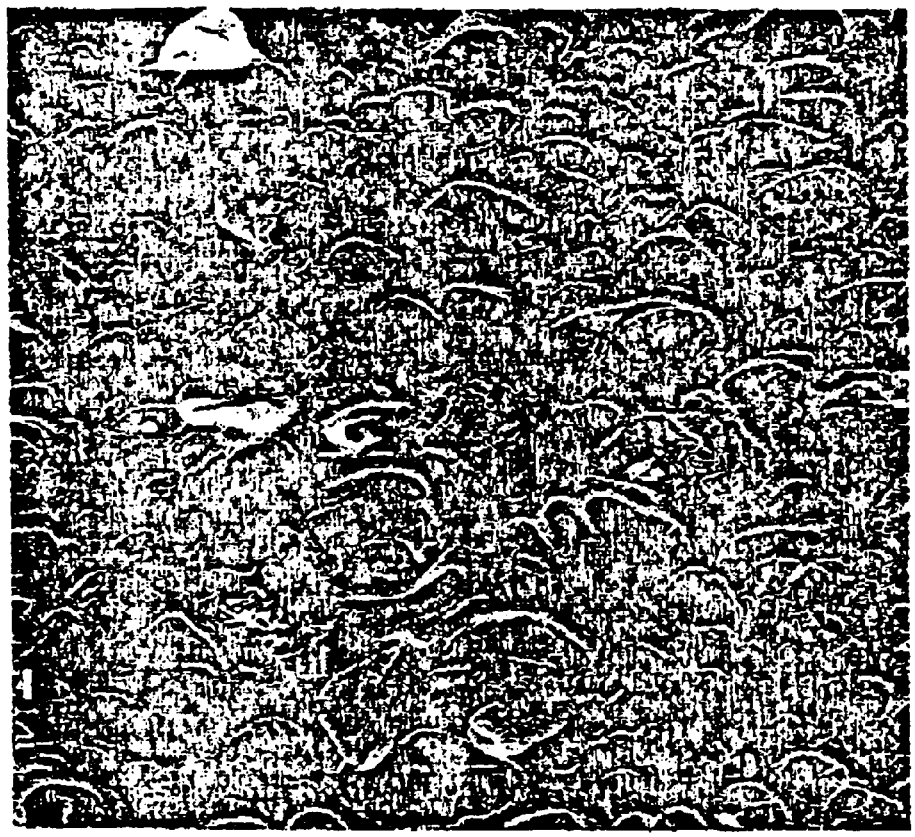

METHOD OF FILTERING A FLUID SUSPENSION WITH A MEMBRANE HAVING A PARTICULAR COATING

RELATED APPLICATIONS

This is a continuation-in-part of U.S. patent application Ser. No. 08/971,887 filed on Nov. 17, 1997, U.S. Pat. No. 5,972,217, which is a continuation-in-part of U.S. Ser. No. 08/810,751 filed on Mar. 4, 1997, U.S. Pat. No. 5,795,483, which is a divisional of U.S. patent application Ser. No. 08/323,559 filed Oct. 17, 1994, U.S. Pat. No. 5,647,985.

BACKGROUND OF THE INVENTION

In processing whole blood for therapeutic administration to patients, it is desirable to separate the various cellular components. In particular, it is desirable to remove leukocytes because of their role in mediating immunologic reactions which can cause adverse clinical events such as allosesitization. For a review of adverse clinical sequellae to transfusion, see Sekiguchi, et al., *Leucocyte-deplated blood products and their clinical usefulness*, Ch. 5, pg. 26–33, from *The Role of leucocyte Depletion in Blood Transfusion Practice* (1988). Furthermore, leukocytes are unessential for therapeutic supplementation of cell deficiencies in patients involving platelets and red cells. Thus, filter systems have been devised for passaging blood cells in order to remove leukocytes while allowing platelets or red blood to pass through for subsequent recovery.

There have been a number of approaches reported for leukocyte depletion. U.S. Pat. No. 4,330,410 discloses a packed fiber mass with leukodepletion properties comprising fibers of cellulose acetate, acrylonitrile, polyamide, or polyester. U.S. Pat. No. 4,925,572 discloses use of a gelatin coating to inhibit red blood cell (RBC) and platelet adhesion. Leukodepletion is accomplished primarily through physical entrainment of the cells in the fiber body, and adhesion of RBCs and platelets results from the gelatin coating. U.S. Pat. No. 4,936,998 discloses a strategy for leukodepletion in which a hydrophilic monomer containing hydroxyl or amido groups and functional nitrogen-containing groups such as primary or secondary amino groups is coated onto a filter matrix of known fibers such as polyester, polyamide, etc.

Modification of fiber surfaces has also been used to obtain materials with improved cell separation properties. For example, U.S. Pat. No. 4,130,642 discloses a packed column in which the packing material comprises an Egyptian cotton which has been de-fatted and bleached so that RBC readily pass through the column.

Some separation strategies involve multiple steps. U.S. Pat. No. 4,925,572 discloses a multistep method comprising an upstream porous element for removal of gels, a second element of finer porosity for removal of aggregated matter, and a final filtration step involving common fibers to which surface tension-reducing and improved wetting are obtained by radiation grafting of biocompatible moieties. Further description of leukodepletion methods is contained in Rikumaru, et al. *Advanced methods for leucocyte removal by blood filtration*, Ch 6, pgs. 35–40, from *The Role of Leucocyte Depletion in Blood Transfusion Practice* (1988).

It is of utmost importance in designing leukodepletion strategies in which one goal is to obtain good recoveries of platelets and RBCS, to achieve separations without activating platelets or complement. It is also important that any coatings utilized to enhance the separations not be leached into solution, since the recovered cells are intended for intravascular administration to patients. One approach embodies a filter composed of a porous polymer material with continuous pore structure having a coating combining a nitrogen-containing functional group with a polyethylene oxide chain having 2–15 repeating units (See Jap. Kokai Patent Application No. Hei 5 [1993]-194243). This material is said to entrap leukocytes while giving high yields of platelets.

The use of polyalkylene oxide polymers is well-known in the construction of biocompatible materials, because of its low biological activity in activating cellular and humoral components of blood, and in stimulating immune responses. However, the inertness of the polyalkylene oxide polymers may also interfere with the degree of separation that can be obtained with cell separation filters, unless combined with functional groups that enhance separation parameters. A suitable combination of coating components has not heretofore been developed which is efficacious for cell separations from whole blood as distinct from semi-purified cell suspension mixtures.

SUMMARY OF THE INVENTION

Most blood available as a source for cell separation is whole, and not pre-fractionated. It generally is packaged in one unit (approximately 350–450 ml) plastic bags and is citrated to prevent clotting. Once blood becomes outdated for use in fresh transfusions, it may be fractionated. It would be highly desirable to be able to leukodeplete and separate platelets and RBC from such blood stores directly and immediately rather than wait until it is partially fractionated.

Accordingly, it is an object of the present invention to provide blood cell fractionation means for removing leukocytes from whole blood while permitting recovery in high yield of platelets, plasma, and red blood cells. It is a further object of the present invention to obtain efficacious cell fractionation through a filter without leaching of coating materials which facilitate the differential separation. It is a further object to be able to coat filters and other cell fractionation means so that permanency is attained without covalent interaction with the filter matrix itself, requiring particular functional groups which may interfere with or defeat the object of differential cell separation. It is still a further object of the present invention to provide an improved plasma or platelet collection apparatus.

To this end, in an embodiment, the present invention provides a method of filtering a fluid suspension having at least one biological cellular component that is characterized by having a nonrigid cell membrane free of a rigid outer cell wall, the cellular component being thereby subject to trauma when stress is provided. The method comprising the steps of: conveying the fluid suspension from a source into a gap defined between a first surface that is located about an axis and a second surface that is concentric with the first surface and that has an attached filter membrane having a coating thereon comprising an insitu condensation product of a first electrophilically active, high molecular weight polyalkylene oxide and a second high molecular weight bifunctional diaminopolyalkylene oxide derivative; and holding the first surface stationary while rotating the second surface and, with it, the filter membrane relative to the first surface about the axis at a selected surface velocity, taking into account the size of the gap, to create movement of the fluid suspension within the gap without substantial trauma to the cellular component for inducing transport of the cellular component from the membrane while the fluid suspension is transported to the membrane.

In another embodiment, a method of filtering filtrate from a fluid suspension having at least one cellular blood component that is subject to trauma is provided. The method comprising the steps of: conveying the fluid suspension from a source into a gap defined between a first surface that is located about an axis and a second surface that is concentric with the first surface and that has an attached microporous filter membrane having a coating thereon comprising an insitu condensation product of a first electrophilically active high molecular weight polyalkylene oxide and a second high molecular weight bifunctional diamninopolyoxyalkylene derivative.

In yet another embodiment of the present invention, a method of filtering a fluid suspension having at least one biological cellular component that is characterized by having a nonrigid cell membrane free of a rigid outer cell wall, the cellular component being thereby subject to trauma when stressed is provided. The method comprises the steps of: conveying the fluid suspension from a source into a gap defined between a first surface that is located about an axis and a second surface that is concentric with the first surface and that has an attached microporous filter membrane having a coating thereon comprising an isopolymer of a high molecular weight tetraacrylatepolyalkyelene oxide polymerized by exposure to radiation; and holding the first surface stationary while rotating the second surface and, with it, the filter membrane relative to the first surface about the axis at a selected surface velocity, taking into account the size of the gap, to create movement of the fluid suspension within the gap without substantial trauma to the cellular component for inducing transport of the cellular component from the membrane while the fluid suspension is transported to the membrane.

In a still further embodiment, a method of filtering a fluid suspension having at least one biological cellular component that is characterized by having a nonrigid cell membrane free of a rigid outer cell wall, the cellular component being thereby subject to trauma when stress is provided. The method comprises the steps of conveying the fluid suspension from a source into a gap defined between a first surface that is located about an axis and a second surface that is concentric with the first surface and that has an attached microporous filter membrane having an irradiated condensation product of a high molecular weight tetraaminopolyalkylene oxide; holding the first surface stationary while rotating the second surface and, with it, the filter membrane relative to the first surface about the axis at a selected surface velocity, taking into account the size of the gap, to create movement of the fluid suspension within the gap without substantial trauma to the cellular component for inducing transport of the cellular component from the membrane while the fluid suspension is transported to the membrane; conveying filtrate through the microporous membrane to an outlet; withdrawing filtrate from the outlet; and withdrawing the cellular component from the gap.

Additionally, the present invention provides a system for filtering a suspension having a cellular component that is subject to trauma when stressed. The system includes a stationary housing body having a hollow interior and an inner surface. Rotor means are provided that are rotatable within the housing body, the rotor means having an outer surface spaced from the inner surface of the housing body. The system includes means for feeding the fluid suspension into the space between the rotor means and the inner surface of the housing body. A microporous filter membrane is disposed on the inner surface of the housing body for passing the filtrate to the inner surface of the housing body. The microporous filter membrane includes a filter membrane having a coating thereon comprising an insitu condensation product of a first electrophilically active, high molecular weight polyalkylene oxide and a second high molecular weight bifunctional diaminopolyalkylene oxide derivative. Conduit means are provided in the housing body in communication with the inner surface of the housing body for collecting filtrate passing through the filter membrane means. The system also includes means coupled to the rotor means for driving the rotor means at a rate selected to establish annular vortices about the rotor means, the annular vortices substantially filing the space between the rotor means and the housing body without causing substantial trauma to the cellular components.

The present invention provides a filter matrix, preferably having a fibrous structure, which is coated with a chemical condensation product, prepared by reaction insitu of a first electrophilically active, high molecular weight polyalkylene oxide, and a second high molecular weight polyalkylene oxide derivative, which is either a tetraaminopolyalkylene oxide or a bifunctional dihydroxy- or diaminopolyoxyalkylene derivative, or combination thereof. Alternatively, in another embodiment, the coating may be an isopolymer of a high molecular weight tetraacrylatepolyalkylene oxide, polymerized by exposure to radiation.

The condensation reaction occurs insitu, i.e. after one polymer is dried onto the fibrous fractionation matrix, the second polymer is then contacted with the matrix, and the condensation reaction occurs spontaneously at a temperature between 5 degrees and about 200 degrees centigrade. The electrophilically active, high molecular weight polyalkylene oxide compound has the general structure Y—PEO—R—PEO—Y wherein Y is a reactive moiety selected from an oxycarbonylimidazole, tresyl-, tosyl-, N-hydroxysuccinimidyl, and p-nitrophenyl-activated esters; acrylates; glycidyl ethers; and aldehydes. The oxycarbonylimidazole leaving group is preferred, as will be apparent from the detailed specification, R is a spacer molecule (a chemical backbone) consisting of either bisphenol A (4,4'-(1- methylopropylidene) bisphenol) or bisphenol B (4,4'-(1-methylopropylidene) bisphenol) and PEO stands for polyalkylene oxide.

In the method of preparing the cell fractionation means of the present invention, a first polymer comprising an electrophilically active, high molecular weight polyalkylene oxide compound, having terminal leaving groups as indicated herein above, oxycarbonylimidazole being preferred, is applied to the surface of the cell fractionation means matrix, then drying the first polymer onto the matrix, followed by applying a second polymer consisting of either a tetraamino-, a diamino- or a dihydroxy-polyalkylene oxide, or combination thereof. The reaction between the polymers occurs spontaneously, and an incubation at a temperature from about 5 degrees to about 200 degrees Centigrade is continued for a time sufficient to obtain substantial completion of cross-linking.

BRIEF DESCRIPTION OF THE DRAWINGS

FIGS. 10a and 10b illustrate scanning electron micrographs of an uncoated PES membrane and a PEO-coated PES membrane illustrating cell binding pursuant to Experiment 7.

DETAILED DESCRIPTION OF THE PREFERRED EMBODIMENT

Figure 1:
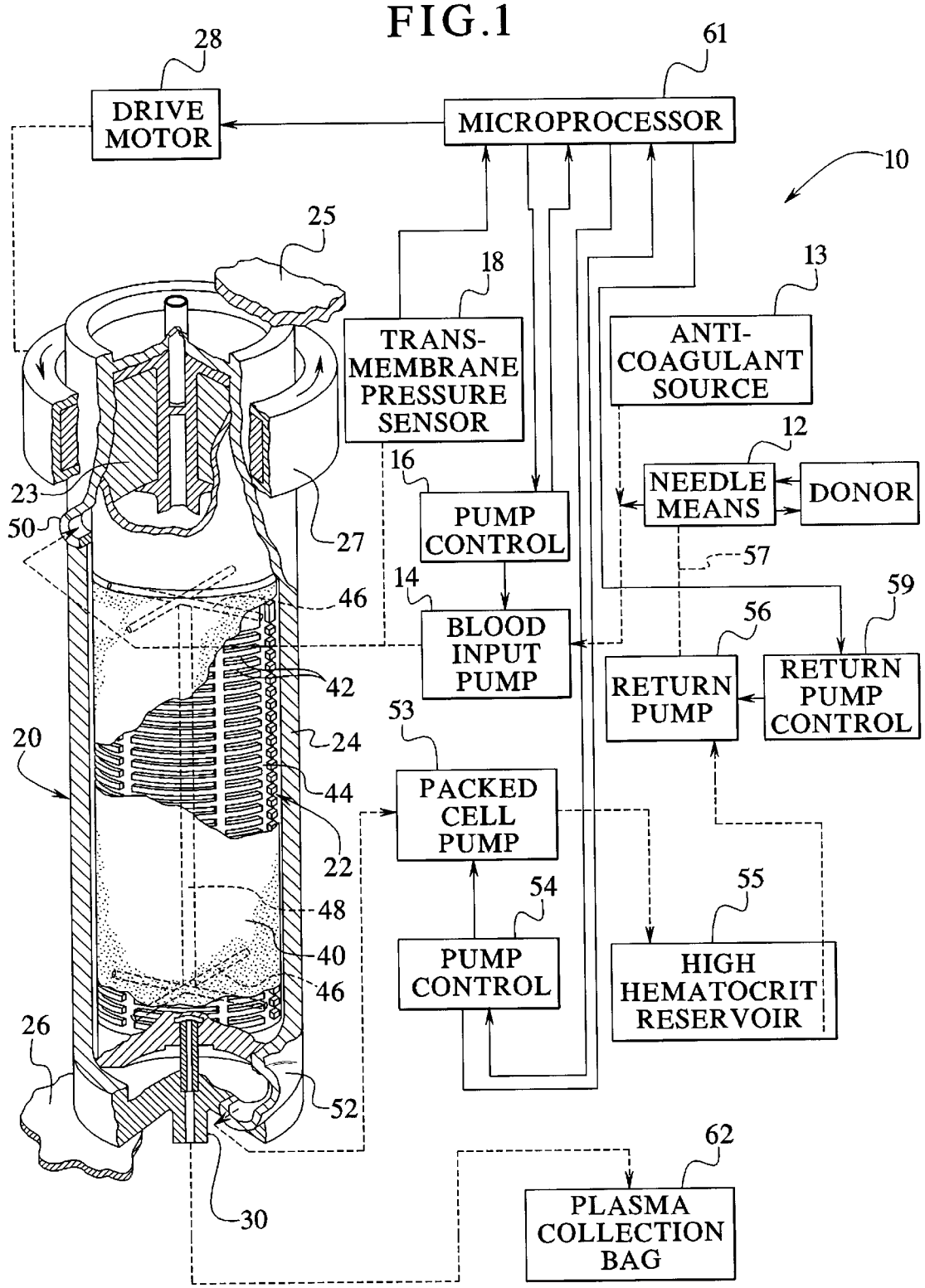
FIG. 1 is a combined perspective view, partially broken away and block diagram of a plasma pheresis system of the present invention.

The present invention comprises a system for concentrating and collecting plasma or platelets. The system includes a matrix having a fibrous structure, and the matrix further characterized in having a coating applied to it which changes its surface properties with respect to cellular adherence of blood cell containing fluid coming into contact therewith.

The use of this type of membrane in plasma or platelet pheresis system provides a number of advantages. These advantages, over traditionally used membranes, include a reduction of plasma protein adsorption (fibrinogen/albumin). Additionally, there is reduced platelet binding after exposure to whole blood. Moreover, there is reduced in-vitro cell adhesion after exposure to whole blood, or in culture. Still further, there is negligible platelet activation and limited complement activation.

Such systems and methods for separating constituents of blood typically subject a thin flow sheet of blood to force for a sufficient time to create a concentration gradient of blood constituents while concurrently establishing high shear across the flow. A moving membrane in contact with the flowing blood and concentric with a spinning axis generates both centrifugal force and high shear on the blood flow through viscous drag. The membrane concurrently filters the desired medium solely from the adjacent flowing mass. Radial migration of cellular matter outwardly causes replenishment of light filtrate at the membrane surface to maintain the concentration gradient despite constant recovery of filtrate. The thin flow sheet is configured as an annulus between a rotating member, concentric about a central axis, and a stationary concentric shear wall, and moves longitudinally between entry and exit regions as well as circumferentially about the member. The filtrate, essentially free of higher density constituents, passes readily through the membrane and via the interior of the rotating member into an outflow path.

Usage of a rotating concentric filtration membrane, of the present invention, that is bounded by a concentric shear wall is applicable to a number of systems for separating liquid suspensions. High rotational rates in association with small gaps generate flow in which a radial concentration gradient and high shear are both obtained.

In a preferred embodiment, the membrane of the present invention is used in a system and in a method such as those set forth in U.S. Pat. No. 5,194,145, the disclosure of which is hereby incorporated by reference. The configuration provides filtration rates in excess of ten times that found in prior membrane filtration devices, for a given surface area. A membrane covered spinner, having an interior collection system, is disposed within a stationary shell, and blood is fed into the space between the spinner and the shell, moving both circumferentially about the shell and along the longitudinal axis to a spaced apart exit region. A device, having a gap of 0.030" and a rotational velocity of approximately 3600 r.p.m., with a spinner diameter of 1" (2.54 cm) and length of 3" (7.5 cm) enables plasma to be derived at approximately 45 ml/min, and with high plasma recovery (e.g., in excess of 70%). A plasma recovery of 0.9 ml/cm$^2$/min is achieved in contrast to prior art flat plate systems providing about 0.039 ml cm$^2$/min and hollow fiber systems providing 0.–013 ml cm$^2$/min.

A further improved system and method for filtering matter from a suspension are provided by establishing an operating regime, in Couette-type flow, in which the radial gap, spinner diameter, and angular velocity are selected for a given liquid suspension to establish strong but controlled Taylor vortices along the length of the spinner. The strong vortex action creates a series of adjacent annular vortex cells about the spinner and moving along the length of the spinner while alternating in direction of internal circulation. The vortex action is strong enough for the cells to substantially fill the radial gap, and matter in suspension thus is impelled in a complex path having orthogonal velocity components at both the spinner and outer wall surfaces. Matter may be filtered via a surface membrane from either the inner (spinner) surface, the outer (stationary wall) surface, or both. The velocity components at the membrane surface contribute meaningfully to the high shear rate established by relative spinner-wall motion and provide an interior sweeping motion within the radial gap that tends to clear the membrane of matter that would otherwise deposit on the membrane pores, as filtrate is rapidly extracted.

Systems and methods in accordance with the invention are particularly useful in overcoming the many and difficult problems of hemapheresis systems, but are equally well suited for a wide range of other applications. The concept appears useful wherever the aggregate viscosity of the system permits establishment of strong Taylor vortices over a length of spinner despite constant filtrate extraction, and the density of solid or particulate matter within the suspension allows entrainment of the matter within the circulating vortices.

In a specific example of a filtration system and method, a vortex action is created that is well above the onset of Taylor cells but below levels at which destructive shear might occur. A membrane covered spinner having an internal filtrate collection system is separated from a concentric outer wall by a predetermined radial gap within which an augmented but substantially uniform vortex action is maintained despite filtrate extraction. Preferably the radial gap is selected to be near the upper end of the permissible range where shear and vortex forces are maximum with the other factors being adjusted accordingly. This insures that the velocity of extraction through the membrane, which tends to draw cells into the membrane, is more than counteracted by the orthogonal velocity components sweeping the membrane surface. The vortex action is not so vigorous that inward flow causes cell deposition on the membrane or outward flow causes excessive turbulence and destructive effects. The counter-rotating vortices constantly mix the matter in suspension, replenishing the supply of potential filtrate available at the membrane surface, adjacent each vortex cell. Moreover, there is substantially constant advance of the cells from input to output, so that local static conditions cannot exist. Filtrate within the suspension is more mobile than the entrained cellular matter or solids and can be interchanged between vortex cells so as to tend to equalize filtrate extraction rates throughout the membrane.

Under conditions of strong, but, controlled vortex circulation, the tangential flow velocities can advantageously be balanced for specific purposes against radial flow velocity through the membrane. In a plasmapheresis system, for example, the transmembrane pressure and the plasma throughput ("% take") are readily determined by instrumentation devices and real time calculations. The transmembrane pressure relative to plasma throughput for a 100% efficient membrane is derived by analysis or empirical observation, to establish a reference identifying the onset of cell deposition. When the transmembrane pressure increases to or above the level at which cell deposition is imminent, separation systems in accordance with the invention reduce the filtrate throughput rate at least for a time. The consequent decrease in filtrate radial flow velocity allows the tangential flow components to free deposited cells or maintain efficiency, thus clearing the membrane and restoring system efficiency.

Other systems in accordance with the invention implant the filter membrane in the outer, stationary, wall with a number of constructional advantages and minimal reduction in operating efficiency. The stationary membrane surfaces may readily be replaced for use of the system as a separator for diagnostic applications, or for applications where the system is to be operated continuously for extended periods. In a specific example of this type of separator, the vortex flow is established by a spinner retained within a concentric split housing that can be opened to replace longitudinal filter membranes. An external magnetic drive rotates the spinner at an angular velocity that insures, relative to the gap and suspension viscosity, that strong vortices exist to provide sweeping action and freedom from clogging at the membrane. With a slightly lower extraction rate than used in an interior membrane system operating with a given spinner surface velocity, a high % take is nonetheless achieved. The velocity or gap dimension can be increased to provide a higher % take in many instances. The system has further advantages if used for diagnostic or analytical purposes because the membrane can be replaced and the unit can repeatedly be reused by rinsing the membrane between operations.

A specific example of a system for providing superior plasmapheresis operation employs maximized gap spacings for a given rotational rate, together with Taylor numbers in the range of 70 to 250 and shear rates of 7500/sec to 10000/sec maximum. Among the further aspects of the invention, pore sizes can be used that are in the range of 0.8 to 1.0 microns, these being larger and more efficient than those heretofore used. In addition, blood flow through the separation device can be against gravity if desired for specific purposes. Inasmuch as minimal membrane area is desired for low cost plasmapheresis disposals, a relatively small range of gap sizes and angular velocities is employed for achieving maximized and constant throughput rates for plasma. For example, with a 1" diameter rotor the gap dimension is held in the range between about 0.018" and 0.030" for rotor angular velocities of 3000 to 3600 r.p.m.

Referring now specifically to FIG. 1, a plasmapheresis system 10 is illustrated. The elements have been depicted only generally, provides a particularly suitable example of a blood separation system in accordance with the invention. Whole blood is taken from a donor via a needle means 12, shown as a single needle although a double needle system may alternatively be used. Disposable tubing is utilized to conduct the blood from the donor, and to combine it with a flow of anticoagulant from a source 13 (flow control for the anticoagulant being of any one of a number of known types and therefore not shown). An input blood pump 14, such as a peristaltic or pressure roller device, feeds the combined flow, when actuated by an associated blood pump control 16, to a transmembrane pressure sensor 18 and also to a disposable plasma separator device 20. The plasma separator 20 is in the form of a spinner 22 having magnetic elements 23 integral with one end and rotatable about a central longitudinal axis within a stationary housing or shear wall 24. The spinner 22 is receivable between a pair of positioning supports 25, 26 spaced apart along the central axis, and shown only generally. The upper support 25, seen only in fragmentary form, provides a positioning seat for a non-rotating upper portion of the separator device 20. At the upper end also a magnetic drive 27 (not shown in detail) encompassing and magnetically coupling to the magnetic elements 23 integral with the spinner 22, is rotated by a drive motor 28. The lower support 26 receives the lower end of the stationary housing 24 and defines an opening through which a plasma outlet 30 coaxial with the central axis may provide plasma as output.

The surface of the spinner 22 may be covered by a filter membrane 40 that is discussed in greater detail hereinafter. Under the membrane 40, the spinner surface is configured to define a plurality of circumferential grooves 42, interconnected by longitudinal grooves 44 which in turn communicate via radial conduits 46 with a central manifold 48. The manifold 48 is in communication, through an end seal and bearing arrangement (not shown in detail) with the plasma outlet 30.

While blood from the donor is fed into the space between the spinner 22 and inner wall of the concentric housing 24 via a tangential blood inlet 50 coupled by a flexible tubing (not shown in detail) to the blood input pump 16. A high hematocrit return flow is taken from a tangential outlet orifice 52 spaced apart from the inlet along the longitudinal axis of the separator device 20. Flexible tubing (also not shown in detail) couples the outlet 52, through a peristaltic packed cell pump 53 operated by a control 54, to a high hematocrit reservoir 55. Separator 20 operation can thereby be isolated from the donor so that alternate pump and return cycles can be used with a single needle device. Packed cells are reinfused in the donor at the needle means by a return pump 56 in a return line 57 between the needle means 12 and the reservoir 55. A return pump control 59 operates the return pump 56 at rates and times determined by the control system, which may include means (not shown) for sensing the level in the reservoir 55.

Preferably a microprocessor 61 is used to monitor various conditions and to establish various controls, so that a number of operating modes can be established and the system can operate automatically with a minimum of operator attention. The principal inputs to the microprocessor 61, for purposes of the present description, are taken from the transmembrane pressure sensor coupled to the output of the blood input pump 14, and the flow rate for packed cell output established by the rate set at the packed cell pump control 54. The flow rates for the packed cell output are derived at the microprocessor 61 by counting the number of revolutions at the pump 53. Other flow rates, and the motor speed if desired, can be fed back to the microprocessor 61, but these need not be described here.

The separator device 20 extracts plasma from the whole blood flow, through the membrane 40. The plasma flows through the membrane 40 into the circumferential and longitudinal grooves 42, 44 on the spinner 22 surface and then into the central manifold 48 via the radial conduits 46. The collected plasma in the central manifold 48 passes through the plasma outlet 30 to a plasma collection bag 62. The typical donor supplies two to three units of plasma in thirty to forty-five minutes, this being a rate consistent with blood supply from and high hematocrit return to the donor, without discomfort or substantial danger. Under proper operation, the plasm is clear and golden in color, being essentially completely free of cell damage and consequent hemolysis.

It is, however, extremely important to achieve maximum reliable throughput of plasma, without trauma to the blood on the one hand or creation of a sensitive or unstable plasmapheresis procedure on the other. Further benefits can then be derived in terms of the efficiency of plasma extraction, possible reduction of the cost of the expensive filter membrane, and the amount of donor time that is required. A strong vorticity is indeed in the form of successive, alternately circulating, annuli about the spinner and occupying the gap between the spinner and the shear wall. This vortex action is of a type, referred to as Taylor vortices, first proposed by G. I. Taylor in 1923 and described by him in *Phil. Trans. Am.*, Vol. 233, pp. 289–293 in "Stability of a Viscous Liquid Contained Between Two Rotating Cylinders." Prior theoretical and computer simulation studies of the Taylor phenomenon (of which there are many) posit that the flow that is created in a Couette structure, under proper conditions, establishes a continuous sequence of annular vortex cells along the longitudinal axis of the cylinder.

The Taylor number, as it is now called, was defined by G. I. Taylor as the product of the Reynolds number and the square root of the gap between the rotor and the housing divided by the square root of the radius of the rotor. The vortices begin to appear, superimposed on the tangential flow induced by the relative rotation, when the Taylor number is greater than 41.3. Many of the investigations in the past have induced relative movement by spinning either the housing or the central mandrel, or both. In the examples given hereafter, only the central mandrel is spun, although the filter membrane 40 may be disposed on the spinner 22 surface or on the stationary cell. It is also feasible to utilize the vortex action and other flow conditions in a variety of other configurations and with other media, as discussed below.

An important consideration is that the entire useful surface of the membrane 40 is made to contribute to the extraction process even though the suspension changes constantly because of filtrate extraction. The vortex action is augmented to the level at which the Taylor number is in excess of 70, and preferably in excess of 100, but usually not greater than about 250, throughout the length of the filter membrane despite the substantial increase in viscosity as plasma is extracted. Because the vortex cells fill the radial gap and sweep the membrane surface in closely tangential relationship, velocity and force components of substantial magnitude adjacent the membrane 40 surface are induced that are orthogonal to the forces induced by rotation of the spinner 22. This circulating motion, coupled with convection along the spinner 22 axis, constantly seeks to remove any adherent cells from the surface of the membrane 40 and replenishes available plasm for filtration through the membrane pores. Any given point on the membrane 40 is swept in a time varying fashion by matter moving in alternately parallel and anti-parallel directions relative to the axis of rotation of the spinner. The circulatory forces that exist thus supplement the shear forces exerted on the blood by viscous drag, tangential to the spinning membrane 40 surface.

At the same time, constant interchanges between adjacent cells take place, for both plasma and cellular components, although the plasma probably is transported longitudinally more readily than is the cellular matter. The interchange tends to substantially diminish any hematocrit gradient across the gap adjacent the spinner 22, although one can observe a color gradient increasing in intensity as one travels from the inlet to the outlet. Nonetheless the system achieves the desired effect of utilizing all incremental areas of the entire spinner 22 with substantially equal efficiency. Because the vortex cells are not static but are constantly moving downwardly toward the outlet 52, any given incremental area on the membrane is sequentially exposed to different vortex forces, militating against tendencies toward buildup of cell deposition. The scrolling motion of the vortex cells to be angularly disposed or slanted relative to the central axis.

The circumferential rotation within the Taylor vortex cell must not impart so high a velocity that movement inwardly toward the rotating spinner impels red cells toward the membrane with sufficient velocity to induce cell deposition on the membrane. On the opposite side, impingement of cells against the stationary outer wall cannot be so vigorous as to induce damaging turbulence. Both of these conditions can occur with strong vortex action within a range of acceptable shear, the consequences on the one hand being clogging of the pores of the membrane with a concomitant increase in transmembrane pressure and a reduction of plasma flux, and on the other the introduction of cell damage and hemolysis.

Another important aspect arising from the existence of the strong vortex action pertains to a technique for clearing the membrane surface of occluding cells, or maintaining efficient operation. In the system of FIG. 1, the transmembrane pressure is sensed by the pressure sensor 18 at the blood input, and a transmembrane (TMP) threshold pressure is selected based upon the sum of three pressure components namely:

A. The centrifugal "pressure" needed to force passage of plasma from the outer edge of the spinner to the center of rotation, is calculated in accordance with the following formula:

$$P_{cent} = \frac{1}{2}\rho (CPM/60 \times 2\pi)^2 (R)^2, \text{ where}$$

p is the density of plasma

R is the radius of the spinner

CPM is cycles or revolutions per minute

B. The pressure needed to overcome pressure drop in the blood being transported through the system. This drop is not a significant factor unless the gap or tubing dimensions are reduced substantially.

C. The pressure drop introduced by the flux of plasma across the membrane. For a typical Gelman polysulfone (0.65 micron pore size) membrane, and assuming a viscosity of 1.5 times the viscosity of water, for which the pressure drop would be 0.15 mm Hg/ml/min, the resistance factor of plasma would be 0.225 mm Hg/ml/min.

The sum of the three pressure components gives a theoretical TMP which assumes that 100% of the effective membrane is functioning properly. The theoretical TMP calculation is, however, dependent on the pump rates, the hematocrit, the rpm and the diameter of the spinner as well as the flow characteristics of the membrane. However, for a 1" spinner, a gap of 0.030" and 3600 rpm, and assuming a hematocrit of 40%, and a take of 70%, a threshold of 148 mm Hg is selected as a basic reference for typical donors. This is a typical threshold level at the separator, without introducing a negative pressure force arising from gravity feed to a collection bag. In practice selection within a range of 135 to 165 mm will typically allow for operation with different donors, membranes and other variables.

If an increase of TMP above the selected threshold occurs, then the membrane may be assumed to be running at less than 100% effectiveness, so that blood cells are being deposited into the pores, or the membrane is acting to bind excessive protein, or both. Protein binding can be avoided by selection of an appropriate membrane for this specific application. However, the membrane is kept at uniform efficiency or full performance, by responsive lowering of the percentage take in one of several different modes of operation. In a steady state mode, where changes are gradual, the operative rate of the packed cell pump 53 is increased in proportion to the TMP change while holding input flow constant. The resulting amount of decrease in plasma flow is controlled so as to reduce the suction effect of the plasma flux across the membrane 40, increasing the significance of the sweeping vortex flows to maintain TMP constant. However, other modes of operation are feasible for specific TMP variations. If TMP rises quickly or a predetermined amount, then % take can be reduced substantially by an incremental amount, so that the tangential vortex cell forces act to dislodge cells or protein from occluded pores. In practice, a 6 mm Hg variation in TMP (approximately 4% increase) can be compensated for by a temporary reduction of 10% in percentage take. Only a temporary reduction in plasma flux is needed, because the cleansing effect is seen very quickly. Sufficient tangential circulation is provided by the unique combination of rotor gap radius and surface velocity to remove lodged cells and proteins in only a few seconds. In other words the cleansing action is vigorous enough to make the great majority of occlusions reversible. If the increase in TMP is too large and sudden, or if the % take reduction is too large (e.g. 70%), the system may simply be shut down and checked.

The function of shear in separation of blood components has been widely studied in the literature, and is regarded as essentially generating a lift force on cellular matter away from the membrane filter in a shear field. An article by Forstrom et al, entitled "Formed Element Deposition Onto Filtering Walls" in *Trans. Am. Soc. Art. Int. Organs*, XXI, 1975, pp. 602–607 seeks to quantify the onset of cell deposition by defining a deposition parameter in the following terms:

$$\sqrt{v}\, U_f / R2S^{3/2}$$

Where v is the viscosity, $U_f$ is the filtration velocity, R is the diameter of the cell, S is the wall shear rate, and $\lambda$ is a concentrate factor dependent upon the hematocrit.

Forstrom et al state that if the value of the deposition parameter is greater than 0.343, cell deposition on the filter will occur if shear alone is the effective agent In actuality, they found, by reviewing empirical studies, that deposition actually occurred in practical devices when the value of the deposition parameter became greater than 0.15. This was determined from published reports at the critical point where filtration velocity begins to decrease due to occlusion of pore in the filter. Systems in accordance with the invention, however, exhibit practical results that are far above the theoretical barrier proposed by Forstrom et al. A filter having 36.9 $cm^2$ of membrane provides a plasma take of 45 microliter per minute, giving a filtration velocity of 0.020 cm/sec (for 75% take of 40% hematocrit blood at 100 ml/min input). Using $\lambda=17$ with a hematocrit at 40, a value of R (the red cell diameter) of approximately 4.2 microns and a shear equal to 7500/sec, the Forstrom et al deposition parameter calculates to 0.594. Filtration without excessive cell deposition under such conditions would not, according to the Forstrom et al studies, be theoretically possible and should be even less feasible when compared to prior empirical work.

Donnelly et al in "Experiments On The Stability Of Viscous Flow Between Rotating Cylinders, VI, Finite-Amplitude," *Proc. Ray Soc.*, London, Volume 283, 1965, pp. 531–546 established that the amplitude of the Taylor vortex varies as the square root of the difference between the Taylor number at the operating rpm and the critical Taylor number. Donnelly et al, however, used a slightly different formulation for the Taylor number where the Taylor number is proportional to the square of the rpm, so that a direct comparison to values derived from the previously stated equation are not feasible. Nevertheless, the amplitude of the vortex cells increases with the Taylor number, the cells forming first at the rotating wall and expanding outwardly to fill the radial gap. When the vortex cell substantially fills the gap the action of viscous drag at the spinner surface provides local circumferential forces that are much greater than comparable forces at the stationary outer wall. The vortex cell circulation provides sweeping movement in the orthogonal direction at both walls, and it appears that this also is greater at the moving wall than the stationary wall. Vortex cell circulation at the outer wall can be increased to the level originally existing at the inner wall by increasing the rotor rpm. Either or both of the walls can include a filter membrane to achieve greater filtration efficiency than flat plate and other prior systems.

Hemolysis is to be avoided or kept to a minimum in plasmapheresis systems in accordance with the invention, but it must be recognized that there is no strictly defined value or limit as to the amount of permissible cell damage. Objective operative criteria, such as the shear level, are not precise determinants of whether an unacceptable level of hemolysis will be introduced in these dynamic systems. Shear limits for flat plate devices were previously considered to be in the range of 7500 sec, but present systems using vortex cell action have operated without significant hemolysis at in excess of 12,000/sec.

Figure 2:
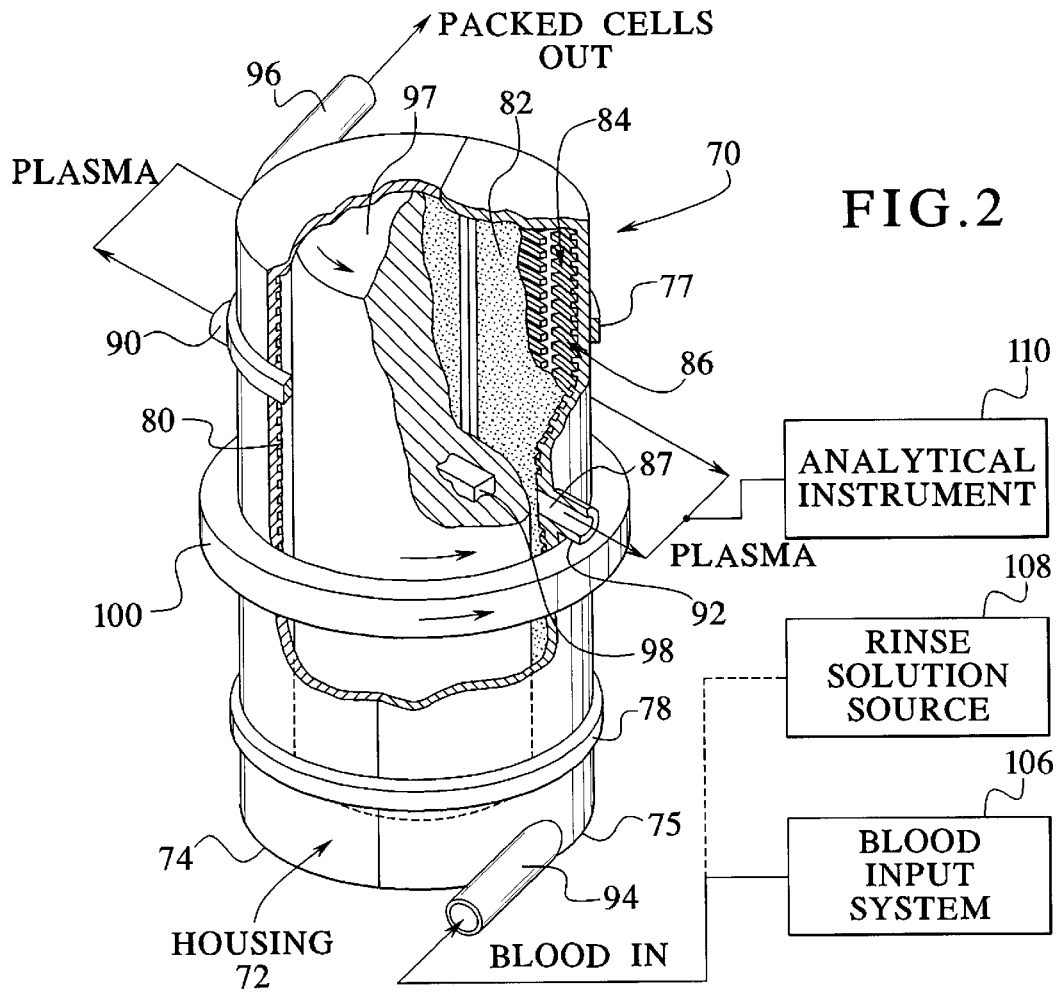
FIG. 2 is a perspective view, partially broken away, of another embodiment of the system of the present invention using a stationary membrane.
Figure 3:
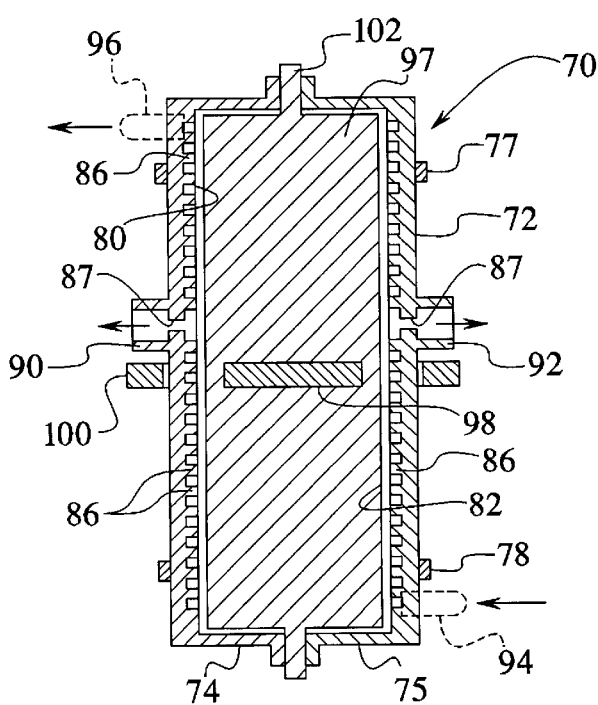
FIG. 3 is a side sectional view of the system of FIG. 2.

The same principles of vortex action may be utilized in conjunction with a substantially different configuration and application, as depicted in FIGS. 2 and 3, to which reference is now made. This comprises a separator device 70 for diagnostic and other analytical applications, wherein small samples may be taken and separated into constituents for individual analysis. The device of FIGS. 2 and 3 also pertains to blood separation, and the usage of separated plasma or serum, although in a diagnostic procedure. However, the principles of construction and operation will be recognized by those skilled in the art as being applicable to other separated constituents and to entirely different liquid suspensions as well.

In the separator device 70 of FIGS. 2 and 3, the cylindrical housing 72 is constructed as a separable member so that access can be had to the interior. In this example the housing 72 is formed as a pair of split halves 74, 75 having integral top and bottom end portions providing a substantially enclosed cell when joined together. The split halves 74, 75 are held together by retainers, such as clamping rings 77, 78. Seals (not shown) may be disposed between the abutting surfaces of the split halves 74, 75 as long as the concentricity of the interior surface is maintained. The inner wall of each split half 74, 75 is defined by one or more removable filter membranes 80, 82 (the structure of which is discussed in detail hereinafter) attached as by a strippable adhesive to the adjacent lands 86 on a network 84 of grooves in the inner surfaces of the housing, these groove networks 84 in each half 74, 75 providing communicating paths through radial orifices 87 for plasma or serum flow between the inner surface of the membrane 80 or 82 and an outlet port 90 or 92, respectively. The outlet ports 90, 92 for filtrate are connected together to provide effluent for fractionation or for analysis by associated instruments. As with the system of FIG. 1, the conduit system under each membrane 80 or 82 provides adequate interconnected flow area to avoid the introduction of substantial impedance to flow of filtrate to the appropriate outlet port 90, 92. The membranes 80, 82 may be removed and replaced by detaching them from the adhesive backing, which need not be strong in view of the fact that the housing 72 and membranes 80, 82 are stationary. However, the adhesive may also be dissolved by chemical means and a new adhesive applied, or a mechanical attachment structure may alternatively be utilized as long as the concentricity of the inner housing face is maintained. It will be appreciated that other types of internally accessible housing structure, including a chemical arrangement, removable end covers and the like, may be employed for different applications.

The whole blood inlet 94 for this structure is coupled tangentially to the housing inner wall at a lower region of the housing, while the outlet 96 is positioned tangentially to the inner wall adjacent an upper end of the housing 72. Within the housing 72 is mounted a cylindrical spinner 97, having an internal magnetic member 98 mounted intermediate its ends. The spinner may be a smooth, plated surface member having an outer diameter providing the chosen gap dimension relative to the inner wall of the housing 72 defined by the membranes 80, 82 and interconnecting housing wall segments. The end surfaces of the spinner 97 are also spaced apart from the end surfaces of the housing 72 by a predetermined amount. The entire housing, in its mid region, is encompassed by a rotatable magnetic drive 100 arranged in operative relation to the magnet 98 within the spinner 97. The drive is positioned with a slight vertical displacement from the magnetic element 98, so as to tend to bias the spinner 97 upwardly and reduce the force of gravity acting against the bottom end wall of the housing. End bearings 102, 103 support the spinner 97 for rotation about the central axis.

A blood input system 106, which may comprise not only a source of whole blood but also a source of anticoagulant and saline solution if desired is coupled to the blood input to the system. A source of a rinsing solution 108 is alternatively coupled to the same input 94, the rinsing solution being substituted manually or automatically for the blood input. Plasma or serum filtered through the system is passed from the outlet 96 to an analytical instrument 110. Typically, the whole blood sample need only be sufficient in size to enable a period of stable extraction of filtrate for a long enough time to obtain an adequate plasma or serum sample (typically in the range of 5 to 30 milliliters).

The operation of the system with whole blood input is again based upon establishment of enhanced vortex flow throughout the entire length of the filter membranes 80, 82. To this end, the magnetic drive 100 synchronously rotates the inner spinner 96 through its magnetic coupling with the magnetic element 98 at a rotational velocity in the range of 3600 r.p.m., it being assumed that the spinner again is approximately 1" in diameter. Using a gap of 0.018 to 0.030", suitably adjusted for blood viscosity and other conditions, vortices are created that fill the radial gap between spinner 97 and housing 72. The existence of vigorous vortices that entirely fill the gap is more critical when the membrane surface is static than in the example of FIG. 1. Because the vortices start near the spinner surface and grow outwardly until they sweep the outer wall it is desirable to insure that viscous damping losses at the stationary wall do not prevent suitably vigorous vortex action at the outer surface. Thus the Taylor number is increased 5–10% over the values previously given for the FIG. 1 system, a by increasing the rotational speed. No hemolysis is observed when this change is made. The centrifugal displacement effects imparted by the rotation of the inner spinner 97 that tend to deposit cellular matter and other heavier matter on the surface of the membranes 80, 82 are overcome by the sweeping vortex motion at the membrane surface.

With stationary membranes 80, 82 about the spinner 97, the system of FIG. 1 can provide successive samples of relatively small amounts of filtrate from inputs provided via the whole blood system 106 from many different sources. In a diagnostic system, where the characteristics of the plasma or serum alone are of concern, contamination is not a problem and the surface cleaning effected by the vortex action can maintain high filtration efficiency for a substantial period of time. Alternatively, saline solution from the input system 106 can be provided between whole blood samples to effect some clearing of the system, or as a further alternative the membranes 80, 82 may be cleaned by use of rinse solution from the source 108. When filtration efficiency drops in unrecoverable fashion below a selected level, the system need only be stopped, the housing 72 emptied, and the housing 72 then opened and new filter membranes 80, 82 used to replace the previously elements.

In the example of FIGS. 2 and 3, passage of whole blood is from a lower input to a higher output, but the essential vortex action and scrolling advance of the vortex cells are unimpeded even though the net flow proceeds upwardly against gravity. As in the prior example the vortices do not remain fixed but translate upwardly in continuous fashion, thus constantly sweeping incremental areas of the surface of the filter membranes.

Referring now specifically to the membranes 40, 80 and 82, and more specifically to the material for construction the membrane, the membrane 40, 80 and 82 comprises a matrix having a fibrous structure with a coating applied to it. The coating changes the surface properties of the fibrous structure with respect to cellular adherence of blood cells containing fluid.

Since the coating of polymers and the chemical reactions which are carried out to create a generally molecularly continuous polymeric surface on the matrix fibers do not require covalent or noncovalent interaction with any chemical moiety present on the native surface of the matrix, the coating itself is independent of the chemical and physical identity of the matrix. Thus, the coating is intended to be universally applicable to any filter and membrane filters available in the cell separation art. Examples include, without limitation, filters having a high glass content, as in glass fiber mats, filters with less or no glass content such as a filter comprising a mixture of glass and polyester, and a polyethylene terephthalate platelet filter coated with hydroxyethylmethyl-methacrylate.

If used in the filter structure, the filter housings for the filter which may be conveniently used are manufactured conventionally. Examples of such housing are Swinney plastic manifolds manufactured by Gelman, pediatric Enterprise Housings, or Intermediate Enterprise Housings. The correct size correlations of filters to correspondingly suitable housings will be apparent to those skilled in the art.

The only limitation applicable to the blood cell fractionation means is a surface which is incompatible with the polymer solutions. Even in the instance where molecular wetting is not obtainable with the polymer solutions, techniques utilizing emulsifiers and phase penetrants may be useful in achieving adequate coating. To Applicants' knowledge, none of the blood cell fractionation filter materials currently available commercially are to be excluded from applicability to the present invention.

For manufacturing ease, chemical condensation reaction of the respective polymers is carried out insitu, i.e. a first free polymer is laid down on the matrix and dried, and then the second is contacted in solution with the matrix. The ensuing reaction then produces a skin-like sheet or layer of copolymerized material at the surface of the matrix. This reaction in the preferred embodiment proceeds spontaneously at temperatures generally in the range of 5 to 200 degrees centigrade. It is evident that the time for completion of the reaction will be slightly longer at cooler temperatures than for higher temperatures in accordance with kinetic thermodynamic principles. Generally, these reactions may be carried out at ambient temperatures, as disclosed in the Examples, but very little experimentation will be required by those skilled in the art to adjust the reaction times to a particular desired temperature of reaction.

The first polymer to be contacted with the filter (as by soaking to saturation) is a high molecular weight electrophilically active polyalkylene oxide. Electrophilically active means that a polyalkylene oxide polymer contains a oxycarbonyl moiety reactive with a nucleophilic center such as an amino or hydroxyl group contained in a second polymer. In a particularly preferred embodiment, a primary amine serving as a nucleophile, reacts with the carbonyl group of the imidazole-polyalkylene oxide polymer to form, upon reaction, an N-substituted carbamate bond where the carbonyl moiety from a cross-linker is incorporated into the new bond. These polymer entities must be high molecular weight, in the range of about 13,000 to 24,000 daltons, preferably about 20,000 daltons. Thus the preferred molecules shown in FIG. 4 for reaction on matrices will have n values of about 100–225. High molecular weight, as herein defined, is important because it was determined empirically that lower molecular weight materials tended to markedly reduce platelet recovery.

Figure 4:
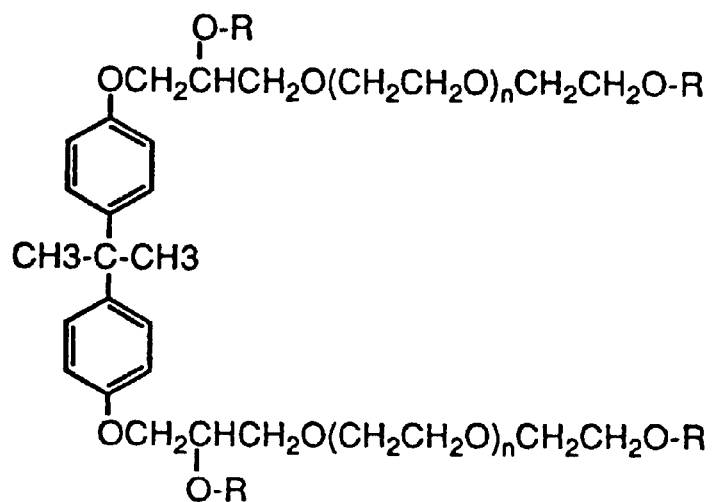
FIG. 4 is a schematic of the chemical structure of the polymers of a preferred embodiment.
Figure 4:
Figure 4:
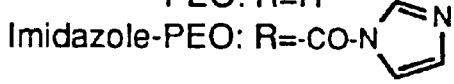
Figure 4:
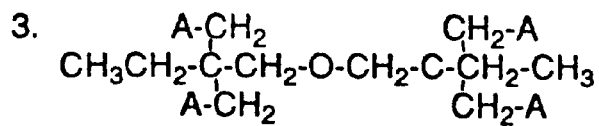

A first electrophilic polyalkylene oxide polymer will have a terminal leaving group reactive with an amine or hydroxyl containing second polyalkylene oxide. Suitable leaving groups on the first polymer for achieving acceptable chemical condensation are imidazoyl-, tresyl-, tosyl-, acryloyl-, and N-hydroxysuccinimidyl-. Additionally the structure of the electrophilic polymer can further be defined by the general expression: Y—PEO—R—PEO—Y, wherein Y is selected from the following group singly or in combination: oxycarbonylimidazole; tresyl-, tosyl-, N-hydroxysuccinimidyl-, and p-nitrophenyl- activated esters; acrylates; glycidyl ethers; and aldehydes, and R is a spacer defined as a backbone to which the two polyalkylene arms are attached, consisting preferably of bisphenol A or B. Bisphenol A is preferred, as shown in the structure of FIG. 4.

We have also determined that the imidazole derived polyalkylene oxides give the best results, perhaps because the reaction proceeds somewhat better, or perhaps because residual unreacted groups improve leukoadhesion. In any event, Applicants do not wish to be bound to any particular theory, but disclose the result as a guide to those experienced in the art. In general, polyalkylene means polyethylene or polypropylene, since these are the most common polyalkylene oxides used in biocompatibility applications. However, Applicants consider other polyalkylene oxides up to polybutylene oxide to be within the scope of the invention.

In a lesser embodiment, a tetra or diacrylate terminal derivative of polyalkylene oxide may be isopolymerized by first contacting with the matrix, followed by irradiation with UV light or gamma rays to effect free radical polymerization. The resulting coated filter matrix is leukodepletive with adequate recoveries of platelets and red bloods cells, but is not a efficacious as the other embodiments of the invention set forth herein.

In the method of the present invention, insitu chemical condensation is carried out to mold the copolymer skin to the contours of the matrix fiber bed. It is important that the electrophilically active polyalkylene oxide by deposited on the matrix first, dried, and then further contacted with the second amino or hydroxy-containing nucleophilic polymer. This teaching arises from empirical observation as to which method steps give best results in terms of platelet and RBC recovery, and leukodepletion, and the mechanistic or molecular basis for the observation is unknown to Applicants. In the drying step, drying in ambient air is adequate to "fix" the polymer in position, but light to moderate heat at various humidities down to less than 5% humidity or in vacuo may be applied to hasten the drying step in a manufacturing context.

The copolymerized material is highly stable to leaching, as shown in the Examples. In contrast to unreacted single polymer labeled with $^{125}I$, which is readily leached into filtrate, the fully copolymerized material made according to the method of the present invention is highly resistant to leaching, and is stable for preparation of therapeutically acceptable cell fractions.

In the method of separating cells according to the invention, a cell suspension or whole blood is filtered through the filter having the polymer coating as disclosed. The leukocytes adhere, and the platelets and RBCs pass through in the filtrate. More generalized methods of contacting the filter with a cell containing fluid are contemplated by this invention as well. For example, contacting by passaging through a packed column, or mixing cells in bulk with dispersed matrix in solution may be employed.

Other advantages of the present invention will be apparent from the Examples which follow.

EXAMPLE 1

Figures 5A, 5B:
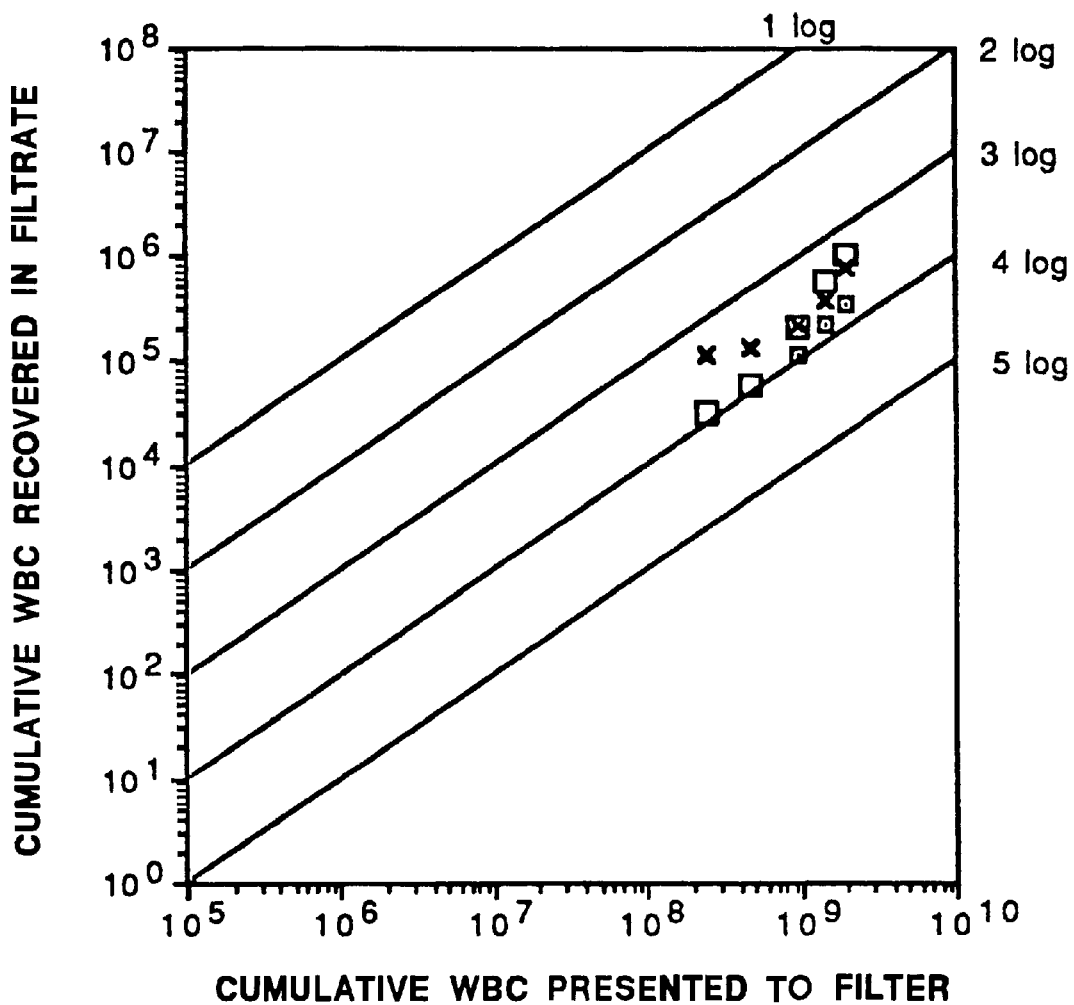
FIGS. 5a and 5b illustrate the relative WBC depletion for PEO-coated and uncoated Asahi R-2000 filters. Log depletion is illustrated on the right side of the figure.
Figures 6A, 6B:
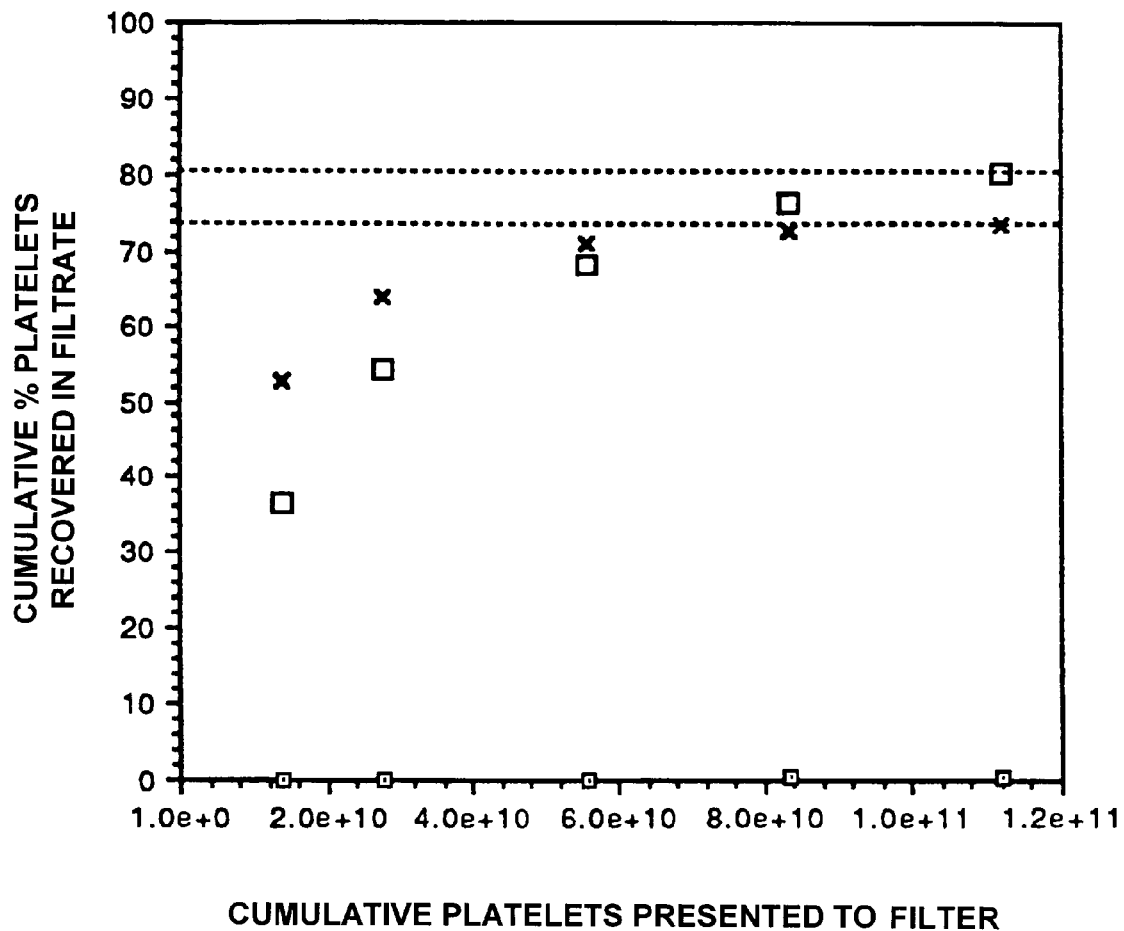
FIGS. 6a and 6b illustrate the relative platelet recovery obtained with PEO-coated and uncoated Asahi R-2000 filters.

Oxycarbonyl imidazole-polyethylene oxide (Imz-PEO) with an average molecular weight of 20 K daltons (Sigma Chemical Company), was first coated onto existing Asahi R-2000 filters by soaking the filter mats in a 2.5% solution of Imz-PEO. The mats were dried under vacuum. The amount of Imz-PEO bound to the mat was about 70 mg/gram of filter mat. Dried Imz-PEO-coated mats were cross-linked with bis[polyoxyethylene bis(amine)] (TAPEO, 20 K daltons), obtained from Sigma Chemical Company. The cross-linking reaction was performed by soaking the Imz-PEO-coated mat in a water-methanol (1:1) solution of TAPEO at a 2.5 to 5.0 fold molar excess over the bound Imz-PEO. The reaction was allowed to proceed for at least 24 hours. The mats were dried again under vacuum. Dried cross-linked mats were washed extensively by soaking with water several times to remove any unbound PEO. After the final wash, the mats were dried again under a high vacuum. Cross-linked mats were stored at room temperature until used for blood filtration. In this example, the mats were used with pooled (ABO compatible), one day old, human whole blood, obtained from Interstate Blood Bank. The pooled whole blood was suspended about 3 feet above the filter unit, and the blood was allowed to flow by gravity through each of the different types of PEO-filter mats. An aliquot of whole blood (20 to 30 ml) was taken from the unit before filtration and was saved as a control (pre-sample). The filtered blood (post samples) and the pre-samples were counted for platelets with a Sysmex K-1000 cell counter and the WBC concentrations were determined by staining WBC nuclei (after lysing the sample) with propidium iodide and analyzing the stained samples with a FacScan flow cytometer. The results of WBC depletion and platelet recovery are illustrated in FIGS. 5 and 6 respectively. The degree of platelet recovery ranged from 75 to 80% with Imz-PEO-coated mats vs 0.5% for the uncoated mats. The amount of WBC depletion remained unchanged, in the range of 3 to 4 logs for all of the mats (Table 1).

TABLE 1

Filtration of Whole Blood Through PEO-Coated and Uncoated Asahi R-2000 Filter Mats

| SAMPLE | WBC Depletion (log) | PLATELET Recovery (% Pre) |
|---|---|---|
| Imz-PEG (no cross-linking) | 3.25 | 80 |
| 2.5x Cross-linked (Mat #1) | 3.39 | 74 |
| 2.5x Cross-linked (Mat #1) | 3.75 | 74 |
| Uncoated | 3.73 | 0.5 |

EXAMPLE 2

In this experiment, variables such as the age of the blood and the storage temperature were evaluated. The same PEO-coated Asahi R-2000 filter mats described above were used for these studies. Units of whole blood were obtained fresh in-house, and stored at room temperature until used (about 2 hours). One day old blood, stored at room temperature or 4 degrees centigrade, were also obtained from Interstate Blood Bank. Each unit was allowed to flow through each PEO-coated filter and the samples were analyzed as described above. The results, summarized in Table 2, suggest that despite the utilization of various units of whole blood stored under different conditions, the yield of platelets obtained from PEO-coated Asahi R-2000 filters is dramatically improved (68 to 83%) as compared to uncoated mats (2%).

TABLE 2

Filtration of Whole Blood Through PEO-Coated and Uncoated Asahi R-2000 Filters

| SAMPLE | WBC Depletion (log) | PLATELET Recovery (% Pre) |
|---|---|---|
| PEO-Cross-Linked Mats: | | |
| Interstate-RT (1 day old) #1 | −2.63 | 83 |
| Interstate-RT (1 day old) #2 | −4.01 | 68 |
| Interstate-4° C. (1 day old) #3 | −3.22 | 80 |

TABLE 2-continued

Filtration of Whole Blood Through PEO-Coated and Uncoated Asahi R-2000 Filters

| SAMPLE | WBC Depletion (log) | PLATELET Recovery (% Pre) |
|---|---|---|
| In-house-RT (~2 hrs) #1 | −3.25 | 76 |
| Uncoated Mats: | | |
| Interstate-RT (1 day old) #1 | −3.50 | 02 |

EXAMPLE 3

In this example, tetraacrylate PEO derivatives were obtained either from Shearwater Polymer Inc., or synthesized from PEO 20 K daltons obtained from Sigma (FIG. 5). The acrylate-PEO derivatives were coated onto composite mats by the same procedure as described in example 1. The dried acrylate-PEO-coated mats were subjected to gamma irradiation at a low dosage (2 megarads) to facilitate cross-linking of the PEO coating. The dried, coated mats were cut into circles of about 1.50 inches, and 3 layers of mats were placed into a small pediatric-sized housing for whole blood evaluation. One day old pooled whole blood, obtained from Interstate Blood Bank was used. The final volume of blood used per housing was about 75 ml. The results of these experiments, summarized in Table 3, demonstrate the improvement in platelet recovery upon coating mats with the PEO derivatives. However, the improvement in platelet recovery seen with the acrylate PEO derivatives is not as good as was observed with the Imz-PEO-coated mats.

TABLE 3

Filtration of Whole Blood Through Various Crylate-PEO-Coated and Uncoated Composite Filters

| SAMPLE | WBC Depletion (log) | PLATELET Recovery (% Pre) |
|---|---|---|
| Uncoated | −2.20 | 43 |
| Sigma-Tetra-Acrylate-20K | −1.62 | 69 |
| Shearwater-Tetra-ACR-14K | −2.04 | 56 |
| Sigma-Tetra-Acrylate-20K Irradiated | −1.64 | 65 |
| Shearwater-Tetra-ACR-14K Irradiated | −1.91 | 65 |

EXAMPLE 4

The stability of these PEO coatings was investigated using radioactively labeled $^{125}$I-Imz-PEO and $^{125}$I-Tetraamino-PEO. The presence of the bis phenol A units in the structure of Imz-PEO or Tetraamino-PEO derivatives permitted conventional labeling of these molecules using $^{125}$I and iodo beads (Pierce Chemical Co.). In the first set of experiments, the $^{125}$I-Imz-PEO was first coated onto the mats and was cross-linked with unlabeled Tetraamino-PEO. In the second set of experiments, unlabeled Imz-PEO was coated onto the mats and then cross-linked with $^{125}$I-Tetraamino-PEO. Each $^{125}$I-PEO-coated mat was evaluated in a Swinney housing (using a filter about 1 cm in diameter) with fresh whole blood. Four fractions of blood filtrate (~1 ml each) were collected and counted for the presence of $^{125}$I-PEO derivatives with a gamma counter. Each $^{125}$I-PEO-coated filter mat was also counted for radioactivity, before and after filtration. The amount of labeled PEO recovered on the mats after whole blood filtration varied from 87% to 95%. In contrast, 35% of the labeled Imz-PEO was leached off filter mats where no cross-linking reaction was performed.

TABLE 4

Stability of PEO-Coated Asahi R-2000 Filter Mats Measured
With $^{125}$I-Imz-PEO or $^{125}$I-Tetraamino-PEO

| SAMPLE with $^{125}$I-Label | $^{125}$I-PEO-Coated Mats Recovered After Filtration (% Pre Labeled Mat) |
|---|---|
| $^{125}$Imz-PEO-Tetraamino-PEO | 95% |
| Imz-PEO-$^{125}$I-Tetraamino-PEO | 87% |
| $^{125}$I-Imz-PEO (not cross-linked) | 65% |

EXAMPLE 5

Various pre and post blood samples from the above experiments were further evaluated for complement activation by measuring C3a and C5a (by RIA) and for platelet activation by determining the percentage of platelets positive for the activation marker CD62. PLS10A platelet filters (Asahi) were included in this analysis as a control for comparison. The results for C3a and C5a is summarized in Table 5A.

TABLE 5A

C3a and C5a Levels in Blood Exposed to PEO-coated and Uncoated
Asahi R-2000 and PIS-10A Filters

| SAMPLE | C3 (ng/ml) Pre-samples | Post-samples | C5a (ng/ml) Pre-samples | Post-samples |
|---|---|---|---|---|
| Cross-linked | 952 | 1,276 | 20 | 54 |
| Cross-linked | 538 | 614 | 0 | 19 |
| Cross-linked | 857 | 1,047 | 17 | 13 |
| Cross-linked | 1,103 | 1,149 | 28 | 34 |
| Cross-linked | 610 | 619 | 15 | 15 |
| Uncoated | 319 | 248 | 29 | 19 |
| Uncoated | 686 | 716 | 15 | 11 |
| PLS-10A | 964 | 4,057 | 22 | 66 |
| PLS-10A | 839 | 2,169 | 33 | 34 |
| PLS-10A | 328 | 1,727 | 9 | 25 |
| PLS-10A | 437 | 2,572 | 4 | 26 |

High levels of C3a and C5a were found in blood samples obtained from Asahi platelet filter PLS-10A. Although these PLS-10A filters have not been used with whole blood, it appears that the PLS-10A produces at least a 2 to 4 fold increase in C3a and C5a levels as compared to the corresponding pre-samples. These levels of C3a and C5a are higher than the amount of C3a and C5a produced by the PEO-coated Asahi R-2000. These results suggest that PEO-coated Asahi R-2000 filters are more biocompatible than the PLS-10A commercial filter used for platelet concentrate.

The percent of platelets expressing the activation marker, CD62, is a sensitive measure of the extent of platelet activation. Samples of whole blood were analyzed (pre and post filtration) using a FacScan flow cytometer to determine the percentage of platelets positive for CD62. This analysis revealed (Table 5B) that no elevation in the percentage of CD62 positive platelets occurred during filtration on any of the mats investigated.

TABLE 5B

Platelet Activation in Whole Blood Samples
Exposed to Various Filters

| SAMPLE | % CD62 in Pre-samples | % CD62 in Post-samples |
|---|---|---|
| Uncoated | 5.45 | 5.88 |
| Cross-linked-PEO | 4.45 | 4.78 |
| Cross-linked-PEO | 5.20 | 5.24 |
| Not Cross-linked-PEO | 5.45 | 3.27 |
| Not Cross-linked-PEO | 4.05 | 2.11 |
| PLS 10A | 5.45 | 2.10 |

EXAMPLE 6

Treatment of Various Membrane Surfaces with
Polyethylene Oxide (PEO) Derivatives Two types of polyether sulfone (PES) flat sheet membranes were used. The first type of membrane (PES-2) was made by casting a solution of polyether sulfone (PES 650), polyethylene glycol (low molecular weight PEG), N-methyl-pyrrolidone and polyvinyl pyrrolidone (PVP) onto a polyester base. The second type of membrane (PES-4) was made similarly to the first but without the PVP in the casting solution and having a base instead of the polyester base.

Each membrane was cut into circles of about 1 cm in diameter. The circles were weighed, and each circle was placed into a well of a 24 well plate containing a 2.5% solution of an oxycarbonyl imidazole polyethylene oxide (Imz-PEO) with an average molecular weight of 20 K daltons. The plate was placed on a circular shaker with a moderate speed, for 30 to 120 minutes, at room temperature. The membranes were removed and dried under vacuum (about 500 millitors) overnight. The amount of adsorbed Imz-PEO was about 70 mg/g of PES-2 and 44 mg/g of PES-4 membrane.

Each circle of dried Imz-PEO-coated membrane prepared above was placed into a well of a new 24 well plate containing a 2.5% water solution of bis[polyoxyethylene bis (amine)] (NH2-PEO, 20 K daltons). A cross-linking reaction was performed at room temperature over the weekend. The cross-linked membrane was removed and dried again under a vacuum. Dried membranes were washed extensively with water to remove any unbound PEO. After the final wash, the membranes were dried again under a vacuum. The total amount of bound PEOs was estimated to be about 20 mg/g of PES membrane. PEO-cross-linked membranes were stored at room temperature until the analysis.

SEM Analysis of PEO-Coated PES Membranes

Figure 7B:
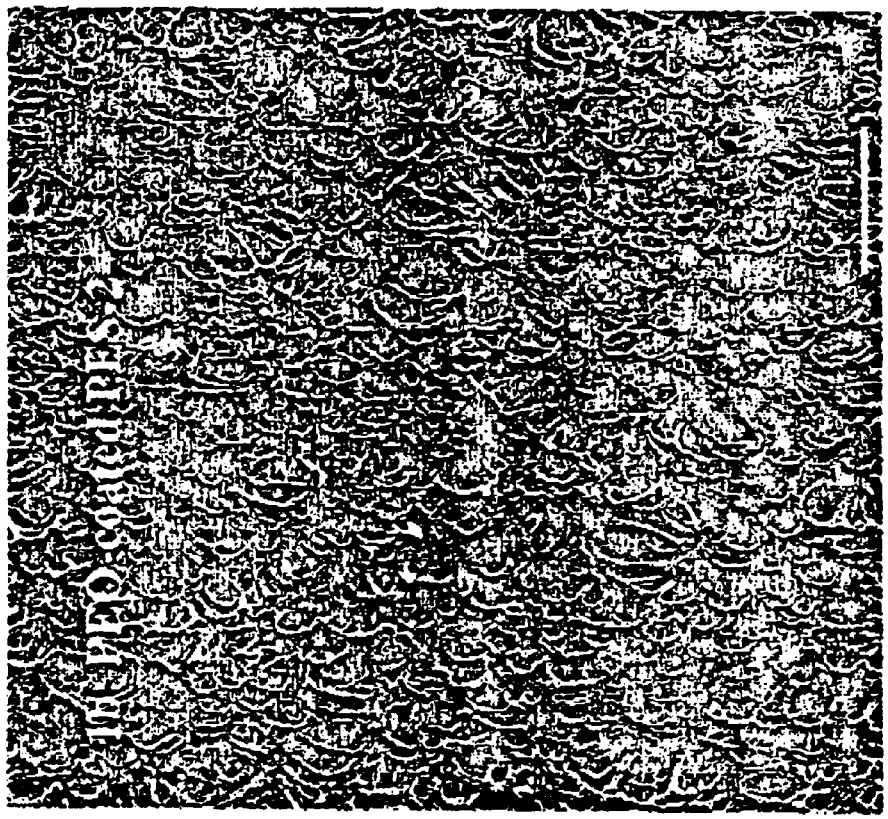
FIG. 7a illustrates a scanning electron micrograph of an uncoated PES membrane and FIG. 7b illustrates a scanning electron micrograph of a PEO-coated PES membrane.
Figure 7A:
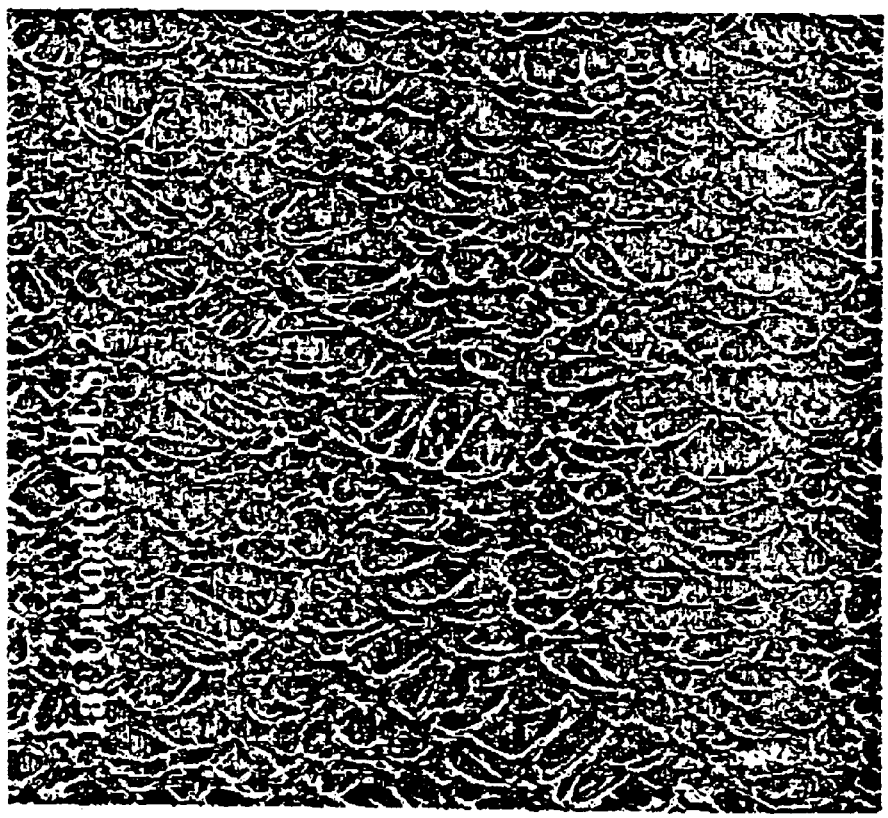
Figures 8A, 8B:
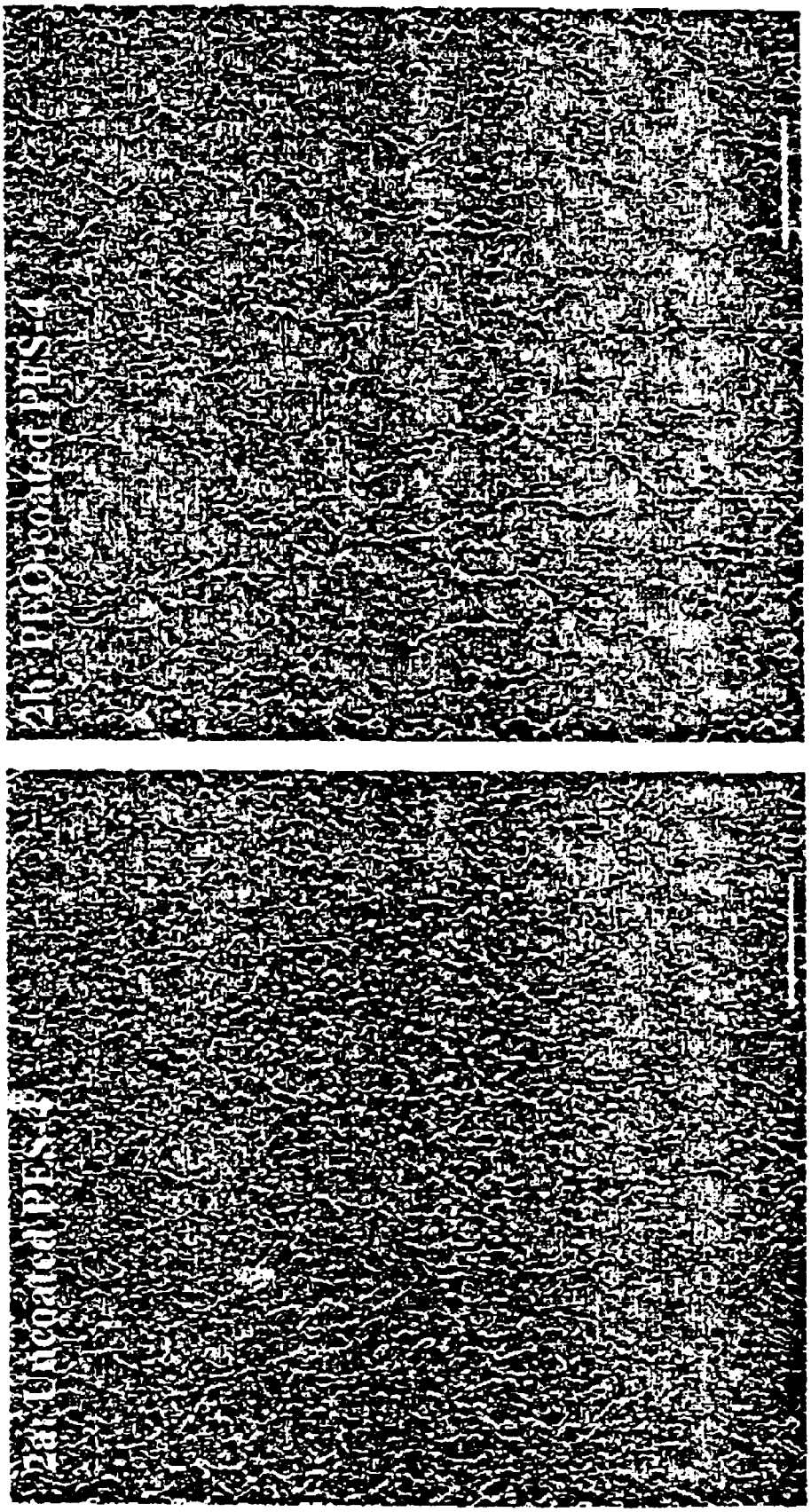
FIG. 8a illustrates a scanning electron micrograph of an uncoated PES membrane and FIG. 8b illustrates a scanning electron micrograph of a PEO-coated PES membrane.

PEO-coated and uncoated membranes were examined using a high resolution Scanning Electron Microscopy (SEM). The homogeneity of the coating was determined by comparing the morphology of the surface before (uncoated) and after coating (PEO-coating). The results of the SEM analysis of PES membranes are illustrated in FIGS. 7a, 7b, 8a and 8b. As shown, the architecture of the surfaces were coated with PEO (FIGS. 7b and 8b) were quiet different from the corresponding uncoated materials (FIGS. 7a and 8a).

EXAMPLE 7

The ability of PEO-coated polymers to interact with whole blood cells was evaluated with fresh whole blood.

1. Effect of PEO Coating on Platelet Adhesion to PES Membranes:

Citrated or heparinized fresh whole blood obtained from healthy donors was divided into three equal fractions. ADP stock solutions were added (1 uM and 10 uM) to the first two fractions to produce blood with activated platelets, and the blood without ADP was used as a non-activated control.

Small pieces of PES membranes, with and without PEO coating, were incubated with fresh whole blood (with and without ADP) at room temperature for 20 minutes in wells of a 24 well-plate. During the incubation, the plate was placed on an orbital shaker set at 250 to 350 RPM. At the end of the incubation, the membranes were removed, washed with PBS and were divided into 2 equal groups. The first group was stored at 4° C. in 1% paraformaldehyde solution and were used for assessing the amount of adsorbed fibrinogen. The second group was stored at 4° C. in 2% glutaraldehyde solution for further analysis.

The blood fractions were analyzed for platelets and WBC with a Sysmex cell counter. The results of platelet recovery in blood samples are summarized in Table 6A. As shown in Table 6A, the level of platelets recovered from blood samples after exposure to PEO-coated PES is consistently higher than in blood samples (with and without ADP) exposed to the uncoated membranes.

TABLE 6A

Effect of PEO Coating on Platelet Binding to PES Membranes with Fresh Whole Blood (% of Control)

| Membranes | PES-2 Uncoated | PES-2 PEO-Coated | PES-4 Uncoated | PES-4 PEO-Coated |
|---|---|---|---|---|
| Donor 1 | | | | |
| no ADP | 78 | 88 | 77 | 87 |
| 1 uM ADP | 90 | 95 | 86 | 102 |
| 10 uM ADP | 86 | 94 | 77 | 89 |
| Donor 2 | | | | |
| no ADP | 92 | 99 | 87 | 104 |
| 1 uM ADP | 96 | 99 | 87 | 112 |
| 10 uM ADP | 91 | 97 | 99 | 112 |

2. Binding of Anti-human Fibrinogen Antibody:

The amount of fibrinogen bound to the membranes (from whole blood) was determined using a mouse monoclonal anti-human fibrinogen antibody (obtained from Biodesign). Membranes that were fixed with 1% formaldehyde were washed with PBS several times before they were incubated with radio labeled $^{125}$I-anti-fibrinogen. The incubation of $^{125}$I-anti-fibrinogen with the membranes was performed at room temperature for 90 minutes. The amount of anti-fibrinogen adsorbed was calculated from the specific activity of the antibody and expressed as nanogram (ng) of protein per surface area or weight (mg) of materials.

The preliminary results (Table 6B) indicated that the PEO coating on both PES membranes resulted in significant reduction in anti-fibrinogen binding. A 7–10 fold reduction was obtained with PEO-coated PES-2 membrane, while only 3.5 fold reduction with PEO-coated PES-4, compared to its corresponding uncoated PES-2 and PES-4, respectively.

TABLE 6B

Effect of PEO Coating on Anti-fibrinogen Binding to PES Membranes after Whole Blood Exposure (ng/cm2)

| Membranes | PES-2 Uncoated | PES-2 PEO-Coated | PES-4A Uncoated | PES-4 PEO-Coated |
|---|---|---|---|---|
| Donor 1 | | | | |
| no ADP | 249 | 30 | 42 | 10 |
| 1 uM ADP | 205 | 17 | 42 | 12 |
| 10 uM ADP | 199 | 26 | 44 | 12 |
| Donor 2 | | | | |
| no ADP | 214 | 32 | 38 | 14 |
| 1 uM ADP | 222 | 27 | 39 | 10 |
| 10 uM ADP | 300 | 29 | 44 | 11 |

3. SEM analysis of cells binding onto surfaces:

Membranes (PES-2) that were fixed with glutaraldehyde were washed with Sorenson Phosphate Buffer (SPB), dehydrated through a graded ethanol series and critical point dried. Mounted samples were sputtered and viewed in the SEI mode on the JOEL 6300F (RLB1021) field emission SEM.

Figure 9A:
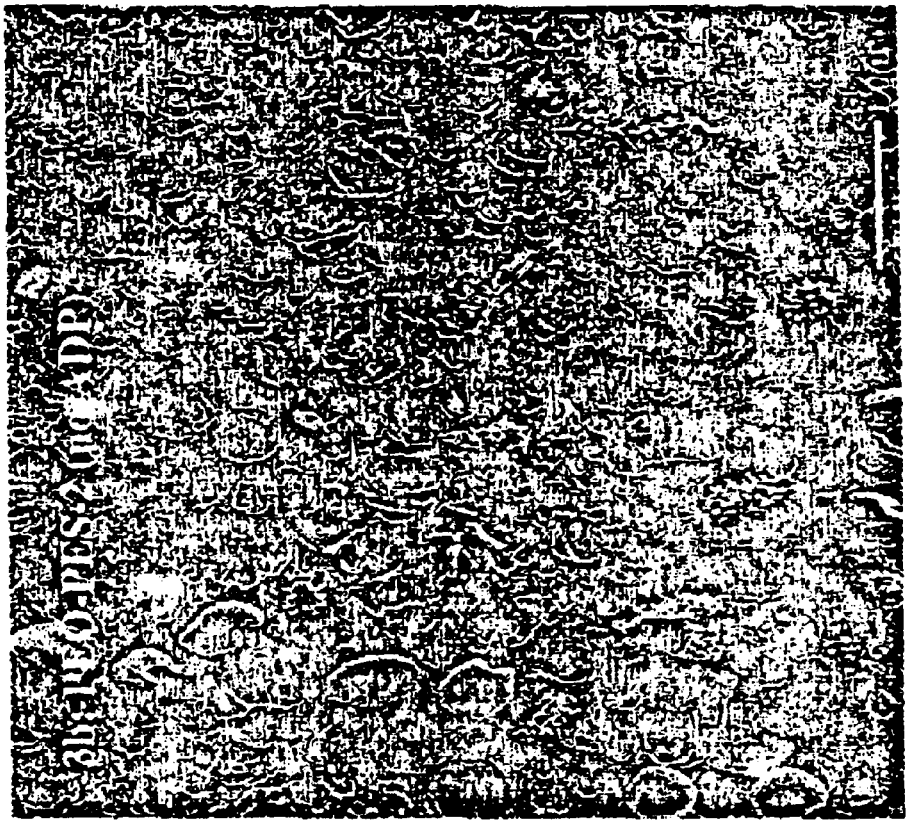
FIGS. 9a and 9b illustrate scanning electron micrographs of an uncoated PES membrane and a PEO-coated PES membrane illustrating cell binding pursuant to Experiment 7.
Figure 9B:
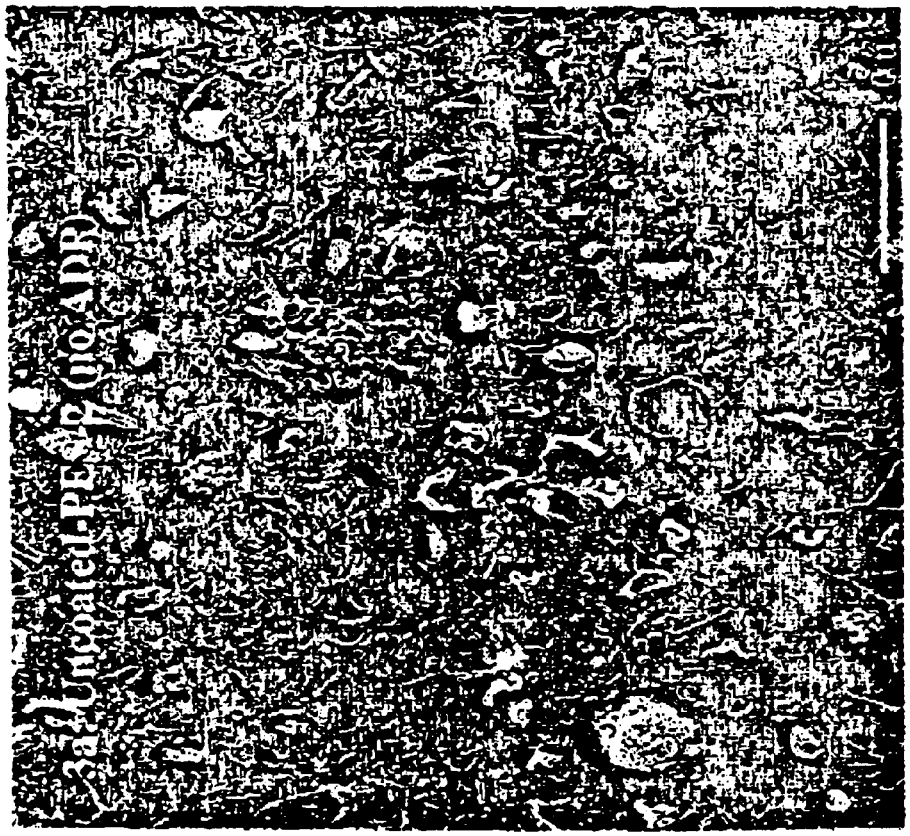

The results of the SEM analysis of these membranes are summarized in FIGS. 9a and 9b (no ADP), and FIGS. 10a and 10 (10 um ADP). As shown in FIG. 9a and 9b, PEO-coated membranes exhibited a very low cell adhesion, compared to the corresponding uncoated membrane, when no ADP was added to blood. With blood containing 10 uM ADP, a number of activated platelets was found attached onto the surface of the uncoated membrane (FIG. 10a), compared to the PEO-coated membrane where only a few cells were found (FIG. 10b).

EXAMPLE 8

The effect of PEO coating on protein adsorption onto PES membranes (prepared in example 7 above) was also evaluated with purified human fibrinogen. Human fibrinogen (Calbiochem) was labeled with $^{125}$1Na (Dupont NEN) using iodo beads (Pierce Chemical Co.) according to manufacturer specification, and was diluted with non-labeled fibrinogen with sodium-citrate-phosphate buffer (CPB) (0.010 M sodium citrate, 0.010 M PBS, 0.01 M NaI and 0.02% NaN3, pH 7.4). The specific activity were adjusted to about 25–30,000 cpm per micro gram of fibrinogen. The coagulability of the radiolabeled fibrinogen was determined according to Paris et al. Reconstitution of the purified Platelet Fibrinogen Receptor. J. Biol. Chem, 260: pp 10698–10707 (1985).

Flat sheet materials (circles of 1 cm in diameter) with and without PEO coating were first rinsed with saline then incubated in the fibrinogen solution for 1 hour at 37°. After incubation, they were rinsed extensively with CPB, then saline solution. Any radioactivity bound to the materials were measured in a gamma counter. The amount of protein adsorbed per unit area (or per weight of materials) were calculated using the known specific activity from the labeled fibrinogen. The results of this binding experiment are summarized in Table 7. As shown in Table 7, all PEO-coated PES membranes exhibit 4 to 5 fold reduction in fibrinogen binding. This result is in agreement with the above finding when anti-fibrinogen was used to assess the amount of bound fibrinogen from whole blood.

TABLE 7

Effect of PEO Coating on Fibrinogen Binding to PES Membranes (ng/mg of sample)

| Membranes | Uncoated (Mean ± SD) | PEO-Coated (Mean ± SD) |
|---|---|---|
| PES-2 | 451 ± 4 | 111 ± 10 |
| PES-4 | 344 ± 10 | 68 ± 4 |

EXAMPLE 9

Other types of flat sheet membranes were also used for treatment with PEO derivatives. They included a polyether terephthalate (PET), polyvinylidene difluoride (PVDF) (Millipore), mixed ester of nitrocelluloses (Millipore), PTFE with polyester backing (Goretex) and Nylon-74 membranes. These membranes were treated with PEO derivatives according to procedures described in Example 6 above. The were all evaluated with the fibrinogen binding assay according to Example 8. The results of these binding experiments are summarized in Table 8. As shown in Table 8, all PEO-coated membranes exhibited a very low fibrinogen binding compared to uncoated materials.

TABLE 8

Effect of PEO Coating on Fibrinogen Binding to Various Flat Sheet Membranes (ng/mg of sample)

| Membranes | Uncoated (Mean ± SD) | PEO-Coated (Mean ± SD) |
|---|---|---|
| PET | 357 ± 23 | 73 ± 11 |
| Nylon-74 | 195 ± 15 | 75 ± 15 |
| Nitro-Cellulose (8) | 3378 ± 267 | 341 ± 153 |
| Nitro-Cellulose - (1.2) | 4329 ± 361 | 293 ± 71 |
| Nitro-Cellulose - (0.45) | 4463 ± 385 | 83 ± 36 |
| PTFE | 454 ± 177 | 28 ± 18 |
| PVDF | 27 ± 2 | 3 ± 0 |

What is claimed is:

1. A method of filtering a fluid suspension having at least one biological cellular component that is characterized by having a nonrigid cell membrane free of a rigid outer cell wall, the cellular component being thereby subject to trauma when stressed, the method comprising the steps of:

conveying the fluid suspension from a source into a gap defined between a first surface that is located about an axis and a second surface that is concentric with the first surface and that has an attached filter membrane having a coating thereon comprising an insitu condensation product of a first electrophilically active, high molecular weight polyalkylene oxide and a second high molecular weight bifunctional diamninopolyalkylene oxide derivative, wherein the polyalkylene oxides can comprise up to polybutylene oxide; and holding the first surface stationary while rotating the second surface and, with it, the filter membrane relative to the first surface about the axis at a selected surface velocity, taking into account the size of the gap, to create movement of the fluid suspension within the gap without substantial trauma to the cellular component for inducing transport of the cellular component from the membrane while the fluid suspension is transported to the membrane.

2. The method of filtering of claim 1 wherein said first electrophilically active, high molecular weight polyalkylene oxide compound has the general structure Y—PEO—R—PEO—Y wherein Y is a reactive moiety selected from the group consisting of oxycarbonylimidazole; tresyl-, tosyl-, N-hydroxysuccinimidyl-, and p-nitrophenyl-activated esters; acrylates, glycidyl ethers; and aldehydes, wherein R is a spacer selected from compounds containing carbon, nitrogen, oxygen, and/or sulfer atoms, and wherein PEO is a high molecular weight polyalkylene oxide.

3. The method of filtering of claim 2 wherein said spacer R is bisphenol A or bisphenol B.

4. The method of filtering of claim 1 including the steps of:

conveying filtrate through the microporous membrane to an outlet;

withdrawing filtrate from the outlet; and withdrawing the cellular component from the gap.

5. A method of filtering filtrate from a fluid suspension having at least one cellular blood component that is subject to trauma comprising the steps of:

conveying the fluid suspension from a source into a gap where the fluid suspension is subjected to high shear across the flow, said gap defined between a first surface that is located about an axis and a second surface that is concentric with the first surface and that has an attached microporous filter membrane having a coating thereon comprising an insitu condensation product of a first electrophilically active high molecular weight polyalkylene oxide and a second high molecular weight bifunctional diaminopolyoxyalkylene derivative, wherein the polyalkylene oxides can comprise up to polybutylene oxide.

6. The method of filtering of claim 5 wherein said electrophilically active, high molecular weight polyalkylene oxide compound has the general structure Y—PEO—R—PEO—Y wherein Y is a reactive moiety selected from the group consisting oxycarbonylimidazole; tresyl-, tosyl-, N-hydroxysuccinimidyl-, and p-nitrophenyl-activated esters; acrylates; glycidyl ethers; and aldehydes, wherein R is a spacer selected from compounds containing carbon, nitrogen, oxygen, and/or sulfur atoms, and wherein PEO is a high molecular weight polyalkylene oxide.

7. The method of filtering of claim 5 wherein said spacer R is bisphenol A or bisphenol B.

8. The method of filtering of claim 5 including the steps of:

conveying filtrate through the microporous membrane to an outlet;

withdrawing filtrate from the outlet; and withdrawing the cellular component from the gap.

9. A method of filtering a fluid suspension having at least one biological cellular component that is characterized by having a nonrigid cell membrane free of a rigid outer cell wall, the cellular component being thereby subject to trauma when stressed, the method comprising the steps of:

conveying the fluid suspension from a source into a gap defined between a first surface that is located about an axis and a second surface that is concentric with the first surface and that has an attached microporous filter membrane having coating thereon comprising an isopolymer of a high molecular weight tetraacrylatepolyakylene oxide polymerized by exposure to radiation; and holding the first surface stationary while rotating the second surface and, with it, the filter membrane relative to the first surface about the axis at a selected surface velocity, taking into account the size of the gap, to create movement of the fluid suspension within the gap without substantial trauma to the cellular component for inducing transport of the cellular component from the membrane while the fluid suspension is transported to the membrane.

10. A method of filtering a fluid suspension having at least one biological cellular component that is characterized by having a nonrigid cell membrane free of a rigid outer cell wall, the cellular component being thereby subject to trauma when stressed, the method comprising the steps of:

conveying the fluid suspension from a source into a gap defined between a first surface that is located about an axis and a second surface that is concentric with the first surface and that has an attached microporous filter membrane having an irradiated condensation product of a high molecular weight tetraaminopolyalkylene oxide;

holding the first surface stationary while rotating the second surface and, with it, the filter membrane relative to the first surface about the axis at a selected surface velocity, taking into account the size of the gap, to create movement of the fluid suspension within the gap without substantial trauma to the cellular component for inducing transport of the cellular component from the membrane while the fluid suspension is transported to the membrane;

conveying filtrate through the microporous membrane to an outlet;

withdrawing filtrate from the outlet; and withdrawing the cellular component from the gap.

* * * * *